United States Patent
Selker et al.

(10) Patent No.: US 9,346,578 B2
(45) Date of Patent: May 24, 2016

(54) ASEPTIC CONNECTORS FOR BIO-PROCESSING CONTAINERS

(71) Applicant: Finesse Solutions, Inc., Santa Clara, CA (US)

(72) Inventors: Mark Selker, Los Altos Hills, CA (US); Barbara Paldus, Woodside, CA (US); Timothy Johnston, Grass Valley, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 0 days.

(21) Appl. No.: 14/292,637

(22) Filed: May 30, 2014

(65) Prior Publication Data

US 2015/0344161 A1    Dec. 3, 2015

(51) Int. Cl.
*B01D 35/00*    (2006.01)
*B65B 55/02*    (2006.01)
*F16L 21/02*    (2006.01)
*B01L 3/00*    (2006.01)
*B65B 5/04*    (2006.01)

(52) U.S. Cl.
CPC ............. *B65B 55/02* (2013.01); *B01L 3/508* (2013.01); *B65B 5/045* (2013.01); *B65B 55/027* (2013.01); *F16L 21/02* (2013.01); *B01L 2200/06* (2013.01); *B01L 2300/06* (2013.01); *B65B 2220/16* (2013.01); *Y10T 29/49828* (2015.01)

(58) Field of Classification Search
CPC .................... A61M 1/00; G01N 1/00
See application file for complete search history.

(56) References Cited

U.S. PATENT DOCUMENTS

| | | | |
|---|---|---|---|
| 3,865,411 A | 2/1975 | Rowe et al. | |
| 4,187,846 A * | 2/1980 | Lolachi et al. | 604/411 |
| 4,673,400 A | 6/1987 | Martin | |
| 6,096,011 A * | 8/2000 | Trombley et al. | 604/256 |
| 6,880,801 B2 | 4/2005 | Matkovich et al. | |
| 7,489,402 B2 | 2/2009 | Selker et al. | |
| 7,695,020 B2 | 4/2010 | Schmidt | |
| 7,824,902 B2 | 11/2010 | Selker et al. | |
| 7,901,934 B2 | 3/2011 | Kunas et al. | |
| 7,954,374 B2 | 6/2011 | Rankin | |
| 7,954,515 B2 | 6/2011 | Gerst | |

(Continued)

FOREIGN PATENT DOCUMENTS

| EP | 2 503 320 | 9/2012 |
|---|---|---|
| WO | WO 2008/016411 | 2/2008 |

(Continued)

OTHER PUBLICATIONS

Hammond, M., et al. (2013) "Identification of a Leachable Compound Detrimental to Cell Growth in Single-Use Bioprocess Containers," In PDA Journal of Pharmaceutical Science and Technology, pp. 123-134.

(Continued)

*Primary Examiner* — Jyoti Nagpaul
(74) *Attorney, Agent, or Firm* — Weaver Austin Villeneuve & Sampson LLP

(57) ABSTRACT

Disclosed herein are apparatuses and methods for installing a sterilized peripheral in a bio-processing vessel. One aspect is an aseptic peripheral connection assembly for installing a sterilized peripheral in a bio-processing vessel via an aseptic connector affixed to the vessel. The aseptic peripheral connection assembly may include a carrier, an applicator, a plunger, and a removable hermetic sealing tab.

29 Claims, 25 Drawing Sheets

(56) References Cited

U.S. PATENT DOCUMENTS

| | | | |
|---|---|---|---|
| 8,491,016 | B2 | 7/2013 | Williams et al. |
| 8,828,202 | B2 | 9/2014 | Feng |
| 8,900,855 | B2 | 12/2014 | Feng et al. |
| 2007/0157748 | A1 | 7/2007 | Baumfalk et al. |
| 2009/0148340 | A1* | 6/2009 | Hansen et al. ............. 422/22 |
| 2009/0151482 | A1 | 6/2009 | Klees et al. |
| 2009/0188575 | A1 | 7/2009 | Williams et al. |
| 2010/0295295 | A1 | 11/2010 | Schmidt |
| 2011/0003380 | A1* | 1/2011 | Miltenyi et al. ............. 435/325 |
| 2011/0062701 | A1 | 3/2011 | Downs et al. |
| 2012/0091326 | A1 | 4/2012 | Baumfalk et al. |
| 2012/0097557 | A1 | 4/2012 | Baumfalk et al. |
| 2012/0132813 | A1 | 5/2012 | Baumfalk et al. |
| 2012/0179052 | A1 | 7/2012 | Wilhelm et al. |
| 2012/0267518 | A1 | 10/2012 | Weisshaar et al. |
| 2013/0092271 | A1 | 4/2013 | Downs et al. |
| 2013/0099489 | A1 | 4/2013 | Williams et al. |
| 2013/0207380 | A1 | 8/2013 | Williams et al. |
| 2013/0289517 | A1 | 10/2013 | Williams et al. |
| 2014/0060675 | A1 | 3/2014 | Wilhelm et al. |
| 2014/0260712 | A1 | 9/2014 | Damren et al. |

FOREIGN PATENT DOCUMENTS

| | | |
|---|---|---|
| WO | WO 2010/017519 | 2/2010 |
| WO | WO 2010/145747 | 12/2010 |
| WO | WO 2011/015270 | 2/2011 |
| WO | WO 2011/066901 | 6/2011 |
| WO | WO 2013/063550 | 5/2013 |

OTHER PUBLICATIONS

Klampfl, T., et al. (Aug. 2012) "Cold Atmospheric Air Plasma Sterilization against Spores and Other Microorganisms of Clinical Interest," In Applied and Environmental Microbiology pp. 5077-5082, aem.asm.org.

Sinha, D. (2012) "Structural Modifications of Gamma Irradiated Polymers: An FT-IR Study," In Advances in Applied Science Research, pp. 1365-1371, Pelagia Research Library, ISSN: 0976-8610.

U.S. Environmental Protection Agency (Nov. 2006) "Ultraviolet Disinfection Guidance Manual for the Final Long Term 2 Enhanced Surface Water Treatment Rule," 436 pages.

U.S. Appl. No. 14/724,659, filed May 28, 2015, Selker et al.

PCT International Search Report and Written Opinion, dated Aug. 25, 2015, issued in PCT/US2015/033057.

* cited by examiner

Prior Art

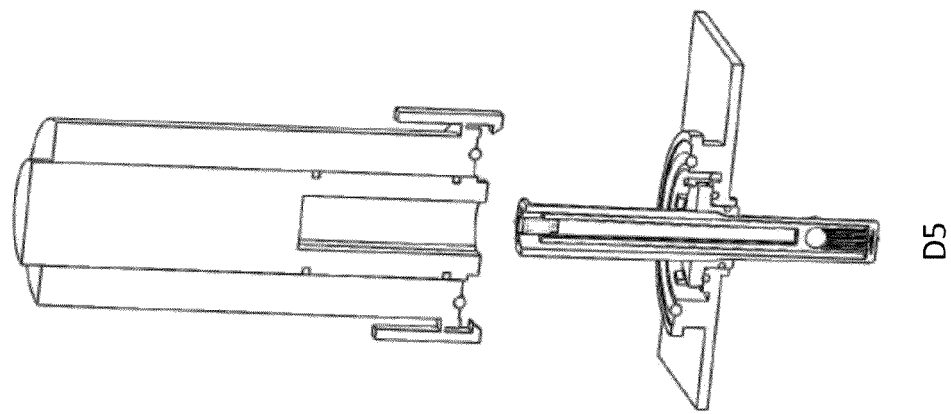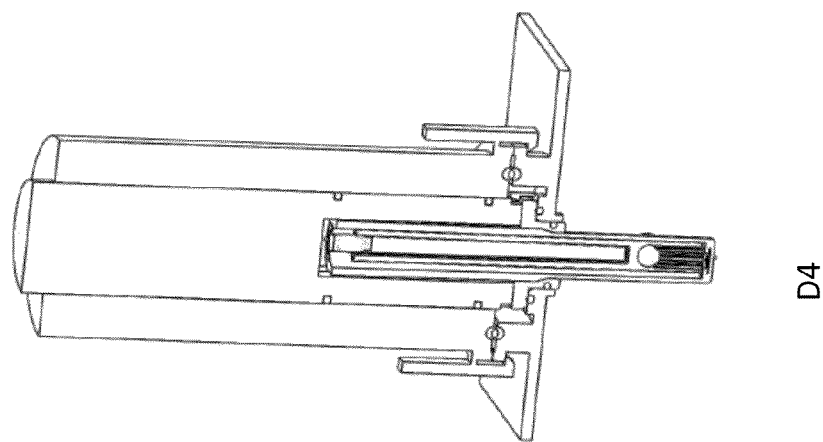
Figure 19

ASEPTIC CONNECTORS FOR BIO-PROCESSING CONTAINERS

BACKGROUND

Over the last few decades there has been a progressive shift to single-use or disposable components in the worlds of medicine and pharmaceutical development/bioprocessing. Much of this shift has been pushed by sterility and health requirements but also by issues such as cost-per-use as mediated by convenience and minimization of labor and overhead considerations. In this context, a sensing apparatus for bioprocessing must not interfere with the benefits of single-use systems.

SUMMARY

Provided herein are apparatuses and methods for installing a sterilized peripheral in a bio-processing vessel. One aspect is an aseptic peripheral connection assembly for installing a sterilized peripheral in a bio-processing vessel via an aseptic connector affixed to the vessel. The bio-processing vessel may be a self-contained container or a flow path. In some embodiments, the bio-processing vessel may be a bioreactor or a filter. The aseptic peripheral connection assembly includes a carrier, an applicator, a plunger, and a removable hermetic sealing tab.

The carrier includes the sterilized peripheral and a sealing member configured to form a leak-tight seal with an aseptic vessel connector on the bio-processing vessel at a location where the carrier is to be installed. The sealing member may include a clip or a ledge. In some embodiments, the sealing member includes an o-ring.

The carrier may be disk shaped with the peripheral having an exposed sensing surface on a flat side of the carrier. In some embodiments, the carrier includes two or more peripherals having exposed sensing surfaces on a flat side of the carrier. In various embodiments, the carrier may be generally sheath shaped with the peripheral having an exposed sensing surface on an end of the carrier.

The peripheral may be configured or designed to detect an optical response. In some embodiments, the peripheral is an electrochemical peripheral, or a temperature peripheral, or a pH peripheral, or an oxygen peripheral. In some embodiments, the carrier includes an oxygen peripheral, a pH peripheral, and a temperature peripheral. In various embodiments, the peripheral is a single use peripheral. The carrier may include two or more peripherals.

The applicator includes a sleeve and vessel-facing opening adjacent to an applicator connector configured to temporarily connect to the aseptic vessel connector on the bio-processing vessel. The applicator may be configured to be removed from the carrier and the bio-processing vessel after the carrier is installed in the bio-processing vessel. The applicator sleeve may be constructed of a rigid material. In some embodiments, the applicator sleeve has a tubular shape and the plunger has a substantially circular shape that forms a seal with an interior surface of the applicator.

The applicator connector may include a clip or a ledge. In some embodiments, the applicator connector may include an o-ring. The applicator connector may be configured to provide a hermetic seal with the aseptic vessel connector while the plunger inserts the carrier into the aseptic vessel connector. In some embodiments, the applicator is composed of polycarbonates, polysulfone, polyvinylidene fluoride, or co-polyester. In various embodiments, the applicator is composed of USP Class VI material that is animal derived component free, latex free, phthalate free, and gamma and e-beam stable.

The plunger is within the applicator sleeve and be configured to plunge the carrier from a position within the applicator sleeve to a position engaged with the aseptic vessel connector to form the leak-tight seal. In some embodiments, the plunger includes an o-ring for forming a hermetic seal with the applicator sleeve while plunging the carrier into position with the aseptic vessel connector.

The removable hermetic sealing tab covers the vessel-facing opening of the applicator sleeve to maintain the sterilized peripheral in aseptic condition prior to installation in the bio-processing vessel. The removable hermetic sealing tab may be configured to be removed from the aseptic peripheral connection assembly after connecting the applicator to the aseptic vessel connector on the bio-processing vessel at a location where the sterilized peripheral is to be installed, and before plunging the carrier from a position within the applicator sleeve to a position engaged with the aseptic vessel connector. In some embodiments, the removable hermetic sealing tab includes a film or sheet having a thickness of between about 1 mil and about 20 mil (thousandths of one inch). The removable hermetic sealing tab may be composed of a simple film if the bio-processing vessel is to be used such that the internal pressure is less than about 1 psig. In some embodiments, the removal hermetic sealing tab may include a USP Class VI, latex free, phthalate free animal derived component free polymeric plate. In some embodiments, the removal hermetic sealing tab is coated with an adhesive.

Another aspect is a bio-processing vessel kit including the above aseptic peripheral connection assembly and a bio-processing vessel housing with the aseptic vessel connector affixed. The bio-processing vessel housing may be a single use bio-processing vessel housing or a self-contained container or a flow path. In some embodiments, the bio-processing vessel housing is configured or designed as a bioreactor or a filter. In various embodiments, the bio-processing vessel housing is a filter with a flow path. The bio-processing vessel housing may be a filter including a container packed with material for product separation.

Yet another aspect is a method of fabricating an aseptic peripheral connection assembly for installing a sterilized peripheral in a bio-processing vessel via an aseptic connector affixed to the vessel by (a) placing the carrier in an applicator; (b) sterilizing the aseptic peripheral connection assembly such that the sterilizing does not employ exposure to radiation at a level of greater than about 15 kGy; and (c) packaging the aseptic peripheral connection assembly in a hermetically sealed package. The aseptic peripheral connection assembly includes (i) a carrier including the peripheral and a sealing member configured to form a leak-tight seal with the aseptic vessel connector on the bio-processing vessel at a location where the carrier is to be installed; and (ii) the applicator including a sleeve and vessel-facing opening adjacent to an applicator connector configured to temporarily connect to the aseptic vessel connector on the bio-processing vessel. The method may further include sending the packaged aseptic peripheral connection assembly to a site for installation in the bio-processing vessel.

In some embodiments, the method may include, prior to (a), applying the peripheral to a carrier structure. The method may include, prior to (a): treating a carrier structure, which does not include the complete peripheral, by a process that reduces colony forming units (CFUs) on the carrier structure; and subsequently applying the peripheral to a carrier structure. In some embodiments, the method may further include calibrating the peripheral in the carrier; and storing information from the calibrating.

The sterilizing further includes exposing the aseptic peripheral connection assembly and packaging to gamma, beta, and/or x-ray radiation. In some embodiments, the sterilizing includes plasma cleaning the aseptic peripheral connection assembly. In some embodiments, the plasma cleaning is performed prior to (c). In some embodiments, the plasma cleaning includes sterilizing using atmospheric plasma at a temperature less than about 40° C. In some embodiments, the plasma cleaning is performed at room temperature. The plasma cleaning may include sterilizing using exposure to non-toxic gases in a plasma. Examples of toxic gases that are not used include formaldehyde and ethylene oxide. An example of a non-toxic gas used in plasma cleaning is air.

The sterilizing may further include exposing the aseptic peripheral connection assembly to gamma, beta, and/or x-ray radiation after the packaging in (c). The packaging may include a vacuum packaging procedure.

The aseptic peripheral connection assembly may further include: (iii) a plunger within the applicator sleeve and configured to plunge the carrier from a position within the applicator sleeve to a position engaged with the aseptic vessel connector to form the leak-tight seal; and (iv) a removable hermetic sealing tab covering the vessel-facing opening of the applicator sleeve to maintain the sterilized peripheral in aseptic condition prior to installation in the bio-processing vessel.

Another aspect is a method of using an aseptic peripheral connection assembly for installing a sterilized peripheral in a bio-processing vessel via an aseptic connector affixed to said vessel by (a) connecting an applicator connector of an applicator to the aseptic vessel connector on the bio-processing vessel; (b) removing a hermetic sealing tab covering the vessel-facing opening of the applicator sleeve; and (c) plunging the carrier from a position within the applicator sleeve to a position engaged with the aseptic vessel connector, and forming the leak-tight seal. The aseptic peripheral connection assembly may include: (i) a carrier including the peripheral and a sealing member configured to form a leak-tight seal with the aseptic vessel connector on the bio-processing vessel at a location where the carrier is to be installed; and (ii) the applicator including a sleeve and vessel-facing opening adjacent to the applicator connector.

Connecting the applicator connector to the aseptic vessel connector in (a) may include providing a hermetic seal with the aseptic vessel connector while plunging the carrier into the aseptic vessel connector. In various embodiments, removing the hermetic sealing tab is performed after connecting the applicator connector to the aseptic vessel connector on the bio-processing vessel, and before plunging the carrier from a position within the applicator sleeve to a position engaged with the aseptic vessel connector.

In some embodiments, the method further includes removing the applicator from the carrier and the bio-processing vessel after the carrier forms said leak-tight seal with the bio-processing vessel. Connecting the applicator connector to the aseptic vessel connector may include providing a hermetic seal with the aseptic vessel connector that is maintained while plunging the carrier into the aseptic vessel connector.

The bio-processing vessel may be a self-contained container or a flow path. In some embodiments, the bio-processing vessel may be a bioreactor or filter. The bio-processing vessel may be a single use bio-processing vessel.

In various embodiments, the peripheral is configured or designed to detect an optical response. The peripheral may be a single use peripheral. The carrier may include two or more peripherals. In some embodiments, the carrier includes an oxygen peripheral, a pH peripheral, and a temperature peripheral. The carrier may be disk shaped with the peripheral having an exposed sensing surface on a flat side of the carrier. In various embodiments, the carrier may be generally sheath shaped with the peripheral having an exposed sensing surface on an end of the carrier. The sealing member may include a clip or a ledge. In some embodiments, the applicator sleeve is constructed of a rigid material. The applicator sleeve may have a tubular shape and the plunger has a substantially circular shape that forms a seal with an interior surface of the applicator. The applicator connector may also include a clip or a ledge.

BRIEF DESCRIPTION OF THE FIGURES

FIG. 19 shows the last two steps in the deployment of the sheath based sensor aseptic connector system.

DESCRIPTION OF CERTAIN EMBODIMENTS

Figure 1:
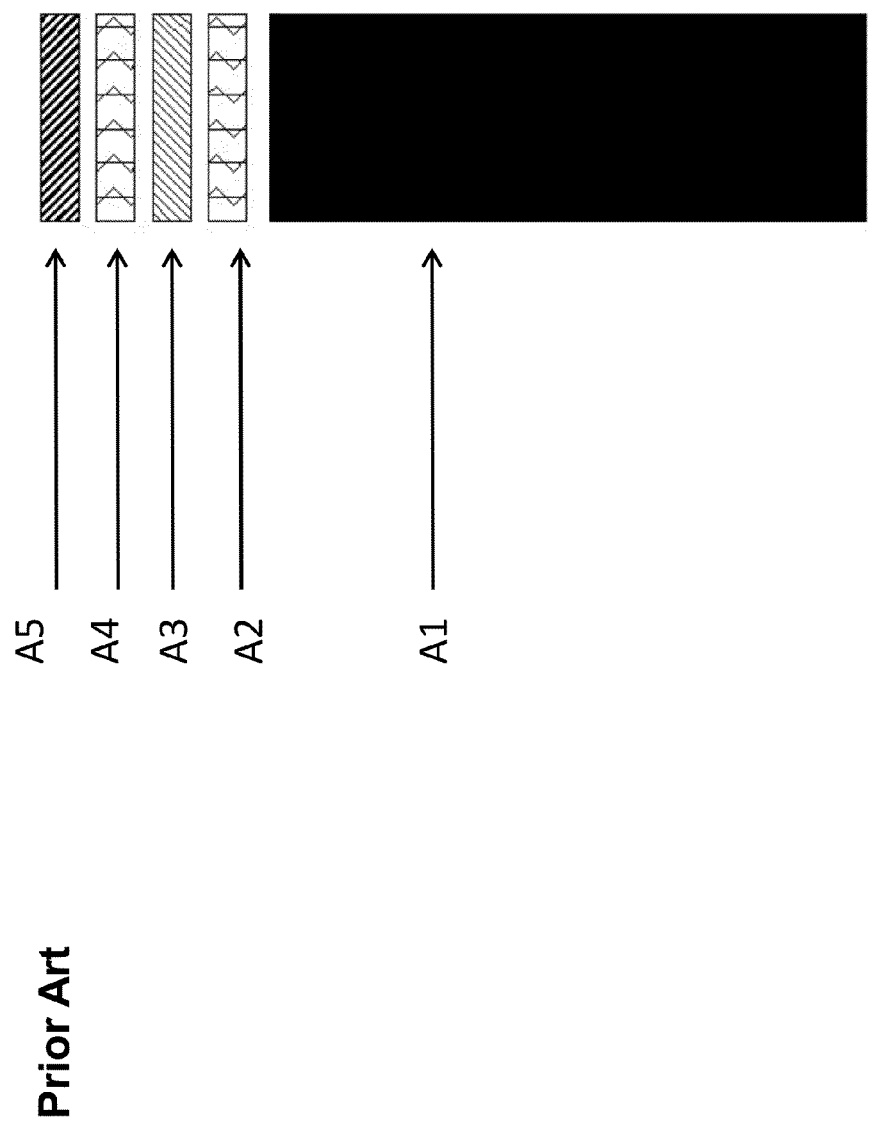
FIG. 1 shows the layer by layer breakdown of a Thermo Fisher bag film.

The bio-processing market has moved rapidly to adopt single-use technology. This move towards the implementation of single-use systems for bio- can be readily understood by considering a typical biotech manufacturing facility. The infrastructure required to implement a facility using traditional glass/steel bioreactors, mixers, and purification systems is substantial, as is the time and expense required to construct the aforementioned facility. The requirement that both the equipment itself and also the ingress and egress tubing utilize inert materials such as 316L electro-polished stainless steel requires a large initial capital investment. Additionally, the bioreactors, mixers (i.e. bio-process vessels) and down-stream processing equipment (e.g. chromatography skids, filtration systems) all have fairly large footprints vis-à-vis available clean-room space and once installed tend to remain in fixed configurations. In contrast, the size and inherent nature of single-use platforms generally permits easier storage and re-configurability when compared to traditional, rigid glass/steel solutions. Other advantages of single-use systems include lower requirements for support infrastructure and time savings over traditional designs. Specifically there is a reduction in preparation and sterilization time, a reduction in the need for purified water, water-for-injection, steam generation and a significantly reduced post-growth-run maintenance time. Additionally, single use systems and their associated plastic tubing lend themselves to being re-configured and validated quickly and efficiently as manufacturing or process requirements change.

As bio-processing becomes more sophisticated in order to reduce manufacturing costs and gain market expansion to geographies with large populations that require significant price reductions, automation will gain in importance. In order to enable cost-effective local production where educated and trained resources as scarce, not only will automation need to reduce operator error and increase batch to batch reproducibility, but it will also need to minimize consumption of raw materials such as media, feed formulations and buffers. Production-on-demand of these materials will in turn limit manual unit operations and increase the level of automation required for the supporting infrastructure in the manufacturing plant. Furthermore, regulatory demands will drive more comprehensive data collection for each batch produced, leading to more complex measurements strategies for each production process step.

All of these drivers will increase the number measurement points to enable better process control as well as more detailed batch records with automated software (rather than operator) driven process alarming, loop correcting, and deviation reporting in the manufacturing execution system layer, and subsequently in automatically generated electronic batch records. Therefore, the insertion of more and diverse sensors into upstream bio-process vessels will be become widespread.

Examples of such sensors in upstream and infrastructure vessels will include:
  pH, dissolved oxygen, temperature, headspace pressure, metabolic parameters such as glucose, cell density and cell viability for bioreactors
  pH, conductivity, temperature, and osmolality for media or buffer preparation mixers
  pH, conductivity and temperature for product holding, mixing, and freeze/thaw vessels Similarly, single-use purification and product isolation skids will also require more measurements points. These downstream process units, however, focus more on flow paths in and out of filters or chromatography columns to process the biological liquids in a continuous stream unlike upstream or infrastructure vessels that retain, recirculate, and/or mix the liquids in a fixed volume. Examples of such "flow path" sensors will include:
  pH, conductivity, temperature, tubing pressure, and liquid flow for filtration skids used for harvest, clarification, virus removal, and ultra/dia-filtration of final product
  pH, conductivity, temperature, ultraviolet response (including spectra) for proteins or anti-bodies and other electronic-chip-based analytics for chromatography steps including product capture with Protein A and product separation using anion and/or cation exchange.

Sensors could also be used in single-use fill-and-finish skids for measurement of liquid flow, syringe filling, and final product purity verification (e.g. spectroscopy such as Raman). Thus, the ability to insert single-use sensors into a single-use process unit operation will be a ubiquitous requirement for the successful implementation of any single-use production facility. As the number of sensors multiplies, the ability to connect them to the process in a robust manner that does not increase the risk of contamination will become paramount.

The term "vessel" generally refers to a self-contained and sterilized liquid container, of whatever shape or configuration, e.g., a cylindrically shaped bioreactor or mixer, or a flow path with multiple junctions and made of pressure-resistant plastic tubing.

Most of this description focuses on single-use bioreactors, but the principals apply generically to any of the aforementioned single-use equipment used in bioprocessing, both in the upstream processing (USP) and downstream processing (DSP) arenas. Examples of USP units include mixers and bioreactors, and examples of DSP tools include chromatography assemblies and filtration skids which may use films similar to those used in USP. DSP tools may implement single-use sensors to replace traditional sensors and/or enable new additional analytical capability. "Smart" sensors for DSP and USP tools may have the capability of being pre-calibrated and gamma- or beta-irradiation sterilized along with the bio-process vessel itself.

Although a number of different styles of single-use bioreactors have been conceived and introduced into the marketplace, two types currently predominate: the "pillow" or "rocker" bag and the stirred tank. The first type of single-use bioreactor to become commercially popular is generally referred to as the pillow or rocker bag style, and is described, for example, in U.S. Pat. No. 6,190,913 the teaching of which is incorporated herein by this reference in its entirety. The pillow or rocker type of single-use bioreactor utilizes a wave motion induced by movement of a bag support platform which generally rocks about a single axis to both mix and sparge (aerate) the contents of the bioreactor. Another of disposable bioreactor is a single-use implementation of the traditional (e.g.: stainless steel and/or glass) stirred tank reactor and utilizes an impeller and a sparger just as its traditional counterpart. The single-use stirred tank implementations include single-use polymeric hard shell bioreactors that functionally imitate small scale glass vessels, and also larger scale single-use versions that generally utilize plastic liner bags that fit inside rigid containers which hold the agitation motors etc. (e.g., U.S. Pat. No. 7,384,783 the teaching of which is incorporated herein in its entirety by this reference). The larger liner bags are typically constructed of multi-layer film laminates that also utilize some form of low or ultra-low density polyethylene (LDPE or ULDPE), ethylene vinyl-acetate (EVA), or similar material generally considered to be inert for the contact layer. The liner type single-use bioreactor vessels (bioreactors or mixers or holding cells for liquids) can be constructed from a variety of different polymeric materials, but as mentioned above, are constructed with an inner layer (i.e., the bag surface which is in contact with the aqueous growth medium) made of LDPE or EVA copolymers. Other materials sometimes used in the construction of the single-use bioreactor vessels include but are not limited to high density polyethylene (HDPE) and Kevlar (Poly-par-aphenylene terephthalamide). By way of example, FIG. 1 shows the construction of the CX-14 film used by Thermo Fisher Scientific for flexible bioreactor vessels. FIG. 1 is obtained from *Thermo Scientific Hyclone BPC Products and Capabilities* 2008/2009. The figure shows Thermo Fisher CX-14 film where the layer in contact with the bio process liquid is A1 (low density polyethylene, 10.4 mil thick) followed by layer A2 (a 0.9 mil thick "tie layer" which bonds A1 and A3), and layer A3 (Ethylene-vinyl alcohol copolymer "EVOH", 1.0 mil thick), and layer A4 (another 0.9 mil thick "tie layer" which bonds A3 and A5), and finally A5 (polyester, 0.8 mil thick).

While single-use bioreactor bags and single-use bioreactor vessels are enjoying popularity, all single use bioprocess vessels (e.g. single-use bioreactors, single-use mixing vessels, single-use liquid holding/storage vessels) are in general seeing increasing market acceptance. To date one major issue has been the lack of robust, single-use sensors that can be readily and reliably integrated into the single-use bioprocess vessel (e.g.: including but not limited to a bioreactor or mixer). By robust, we mean accurate; gamma, beta, or x-ray radiation stable; and capable of being used for real time sensing (real time within the speeds or time responses required for bioprocessing) e.g. providing samples at 1 Hz (or fractions of a Hz to a few Hz) for biological process monitoring and/or control for at least 21 days without significant drift in any 24 hour period.

Single use sensors are generally introduced into these larger stirred single-use bioreactors through lateral ports or simply attached to an interior surface. Currently, a popular way to introduce optical single-use sensors into single-use vessels is through the use of lateral ports. These ports rely on either a "friction fit" (surface to surface contact between their surface area and the single use sensor without a bonding agent to retain the single-use sensor element) or a classic-o-ring. The ports can be constructed from a rigid base and a flexible piece of tubing, or an entirely rigid structure which then relies on o-rings to maintain a seal, or the ports can be constructed entirely from a flexible material (see, e.g., US 2009/0126515 A1, which is incorporated herein by reference in its entirety). Another way single-use sensors are introduced into single-use vessels is to simply adhere them to the innermost surface layer of the vessel and then both illuminate through bag material and collect fluorescent light the same way. Irrespective of how the optical single-use sensors are introduced, they need to be exposed to the contents (therefore inner area) of the vessel in order to measure the analyte concentrations of interest.

At this point it is valuable to review in detail the process of introducing "peripherals" to a single-use bioreactor. Peripherals here mean anything introduced into the single-use vessel using a port. Typically, a peripheral directly supports a function of the bio-processing vessel in which it is inserted. Common peripherals include but are not limited to single use sensors, filters, tubing, and sampling ports. As can be appreciated, peripherals come in various shapes, sizes, and materials of construction. However, many of them are designed for a single use and for insertion into a bio-processing vessel via a port, which may have a standard configuration. The process of adding peripherals through a port is desirable in both rigid and semi-rigid single-use vessels as well as flexible vessels. The addition of peripherals this way is useful as the materials used for the construction of sensors, filters, etc. are generally not made of polyethylene and therefore cannot be simply welded or bonded to the vessel in the way the films themselves are welded together. In general there are a very limited number of materials which can thermally bond to polyethylene. Therefore, a method which allows a convenient aseptic connection to be made will be applicable in the construction of single-use bioprocess vessels. The aseptic peripheral assembly apparatus and methods described herein apply generally to any peripheral device for bioprocessing vessels. In other words, the disclosed assemblies are not limited to sensors.

Figure 2:
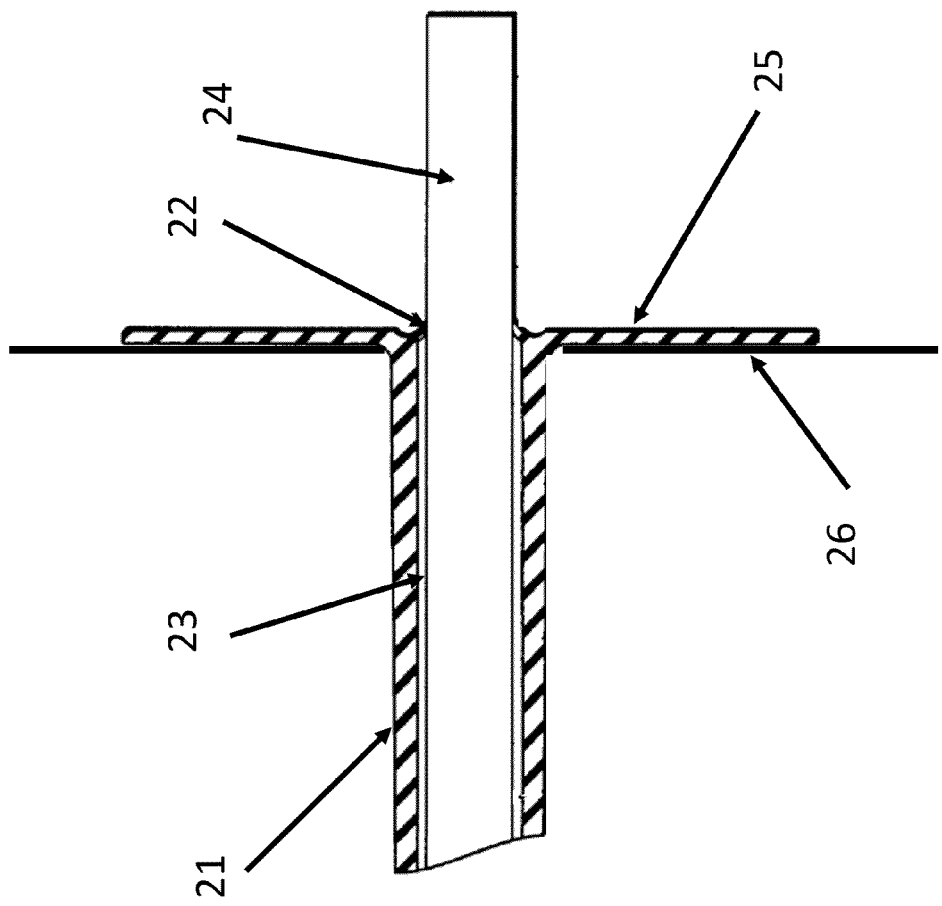
FIG. 2 shows a port design with a seal based on a friction fit.

For a rigid single-use bio-process vessel there are similar material issues and therefore a port; typically a port with an o-ring is utilized to introduce single-use sensors. When starting the construction of a flexible film based single-use vessel, the films are cut or punched according to design drawings and are thermally bonded (e.g. melted together). However, as many of the elements are of dissimilar materials and cannot be readily bonded together, therefore the single-use industry has almost universally adopted the use of ports or flanges in order to add tubing, sensors, sampling sites etc. FIG. 2 shows a picture of a flexible port 21 used by Thermo Fisher to introduce peripherals. It is instructive to note that the base 25 of this port 21 is thermally bonded to the inner layer of the flexible bag 26. The probe, 24, is inserted through the port body, 23, and a seal is made by a molded in flange, 22, which replaces an o-ring. Typically the ports that are welded to the bags are also some form of polyethylene and can be constructed in flexible formats or rigid formats depending on the exact application. As the ports are polyethylene based or compatible material, they can be thermally welded to the film material or over-molded on a flexible single-use vessel. Other vendors utilize rigid ports with a similar overall design but utilizing one or more physical o-rings make the seal.

Peripherals like the vent filters for example are added by connected tubing between the hose-barb ends of the rigid ports and the vent filters. Tubing is often very difficult to slip over the hose barb and requires a lubricant, or more specifically a substance to temporarily change the surface tension such that the tubing can be slipped over the hose barbs. The tubing is then typically secured with 2 tie-wraps that are put on in opposite directions to ensure that the tubing is not pinched and therefore forms a hermetic seal. The substances used to provide the temporary change in surface tension allowing the construction to occur is typically isopropyl alcohol and water (70%/30%) mix or pure isopropanol. Pure isopropanol is typically viewed less by manufacturing organizations as it is flammable, must be transported on the ground (e.g. trucking) and the vapors can be dangerous making it difficult to deal with in a controlled environment. The use of isopropanol water mixes and/or isopropanol in the construction of single-use bioprocess containers is a standard and ubiquitous practice. There is often a sizable accumulation (tens of milliliters or more) of these substances inside the container when the construction process is complete. As single-use (flexible or not) vessels are then double wrapped within 2 or more bags for use in cGMP (Good Manufacturing Practice) qualified applications, the bags are clearly hermetically sealed and the isopropanol/water mix or isopropanol is locked into the vessel during the gamma sterilization process.

The subsequent gamma sterilization of the closed container with these substances locked inside creates other more chemically active substances. For example, when water is exposed to Gamma radiation (Gamma Hydrolysis) it is broken down and forms hydrogen, hydroxyl radicals, and $H_2O_2$ (hydrogen peroxide) and peroxide radicals (LaVerne, J. A., Radiation Research 153, 196-200, (2000)). It is also clear that the exposure of isopropanol ($C_3H_8O$ or $C_3H_7OH$) to Gamma radiation will lead to an even greater formation of highly reactive $OH^-$ radicals (J. Environmental Eng. Management, 20-30, 151-156 (2010)). This means that there are reactive agents (e.g.: solvents) inside the single-use vessel that were never considered, let alone tested in the USP Class VI (United States Pharmacopia) testing regimen or considered by the BPSA, Bio-processing Systems Alliance, (bpsalliance.org) sub-committees on single-use vessels or sensors. Neither $H_2O_2$ nor the post gamma isopropanol compounds are conducive to cell growth and are likely detrimental to any active element (e.g. an opto-chemical sensor) inside the bioprocess container.

These reactive compounds have implications to sensing elements that are introduced into the single-use vessels. Potentially detrimental reactive compounds are formed in all or the majority of the currently employed single-use vessels where water vapor, oxygen, and plastics are present. While the concentration of these reactive compounds created in each material and how these levels scale with surface area and content (e.g. water, isopropanol, etc.) may not be known, clearly the problem exists in many contexts.

Most, if not all, single-use components for bioprocessing are currently sterilized using Gamma radiation or Beta radiation. The requirements for sterilization are in part mandated by the International Standards Organization (ISO) release number 11137-2, which is incorporated herein by reference in its entirety, (ISO 11137: iso.org/iso/catalogue_detail.htm?csnumber=51238).

This standard stipulates the radiation level and requires a particular reduction in the number of colony forming units (CFU) of bacteria. Typical levels of gamma radiation for cGMP manufacturing applications are 25 kGy to 40 kGy and statistical studies on the number of CFU's performed each quarter. However, many in the bioprocessing industry are calling for, or have called for, higher levels of gamma radiation in order to be certain that the level of bacteria and adventitious agents is low enough. The calls for increased levels of gamma radiation have often been for assemblies of single-use components so that there is increased margin on meeting standards such as ISO 11137-2 mentioned above.

While Gamma radiation is a very convenient and effective method of sterilization especially for single-use components in the pharmaceutical, medical, and biotech fields, it has quite a few unintended side effects aside from those mentioned above. Even at 25 kGy there are many fundamental deleterious effects on the materials used to construct single-use components. These include but are not limited to cross-linking of polymers so that they become brittle and can break or leak during use, the creation of color centers or other material level defects that affect the color (e.g. the absorption spectrum is modified), and fundamental changes in material properties (*Structural Modifications of Gamma Irradiated Polymers: AN FTIR Study, Advances in Applied Science Research*, D. Sinha, 2012, 3, (3):1365-1371, incorporated herein by reference in its entirety). Additionally, recent research has shown that materials like low density polyethylene which were heretofore considered completely safe and "pristine" for applications as containers for materials or for bioreactor liners are not as inert after exposure to gamma radiation as had been previously considered. In fact, a recent publication (*Identification of a Leachable Compound Detrimental to Cell Growth in Single-Use Bioprocess Containers*, Hammond et al., PDA Journal of Pharmaceutical Science and Technology, Vol. 67, No. 2, March-April 2013, incorporated herein by reference in its entirety) shows without equivocation that the aforementioned CX-514 film exhibits detrimental characteristics to cell growth following exposure to gamma radiation. The paper identifies compounds such as anti-oxidants (e.g. tris(2, 4-di-tert-butylphenyl)phosphite) which are present in many formulations of polyethylene as responsible for at least some of the issues noted in the field. The paper identifies byproducts (e.g: (bis(2,4-di-tert-butylphenyl)phosphate (bDtBPP)) of these anti-oxidants that are created by gamma radiation process. The gamma radiation breaks down the anti-oxidant that remains in the LDPE; often the anti-oxidant is not completely consumed during the rolling of the films. Hammond et al. showed that bDtBPP can inhibit cell growth for many lines of commonly used cells in biotech drug development. Another byproduct of the gamma radiation exposure of the anti-oxidant noted in Hammond's paper is Phosphoric Acid. It is clear that depending on the surface area of the vessel and the sensitivity of the active elements introduced, many deleterious effects will be endured. However, even before this paper by Hammond et al. was published, it was commonly known that polyethylene films can give off hydrogen when gamma irradiated and that this could interact with ozone that is also created when oxygen is present during the gamma process. As most bio-process containers/bioreactors are closed vessels that are not under vacuum during the sterilization process it is quite possible for Phosphoric Acid, Hydrogen, ozone, and Hydrogen Peroxide to exist simultaneously in the same volume. It is also likely that aggressive free radicals are also present in the single-use vessels immediately following gamma sterilization depending on the exact materials used and the conditions in the vessel during gamma exposure.

In addition to the titer or viability of the cells being directly reduced by the presence of free radicals and radiation byproducts, these byproducts can also affect active elements (e.g. sensors) introduced into the single-use bags prior to gamma exposure. In fact, has been noted by many in the field that single-use optical sensors for analytes such as dissolved oxygen (DO), pH, dissolved $CO_2$ ($dCO_2$), and others are deleteriously affected by exposure to gamma radiation in single-use bioprocess containers. The gamma exposure affects the sensors via two distinct readily delineated mechanisms. The first is the chain scissioning (sterigenics.com/crosslinking/crosslinking htm) of molecules when exposed to the gamma radiation and the second appears to be a surface mediated effect which impacts the spots during construction of the container and during gamma radiation exposure inside the container.

With this background information it is instructive to review the usage case for single-use sensors in this arena. The most common currently deployed single-use sensors for analytes in the single-use vessels are optical sensors for measuring dissolved oxygen (DO), pH, and dissolved $CO_2$ ($dCO_2$). These quantities are often measured using sensors which are based upon the principles of phase fluorimetry. The sensors spots are most commonly constructed using dyes and/or metal inorganic compounds that behave optically like dyes (Lakowicz, *Principles of Fluorescence of Spectroscopy*, $3^{rd}$ edition, Springer 2006, incorporated herein by reference in its entirety). These substances are coated on small (typically ~3-7 mm diameter) optically transparent disks of polyester or mylar or similar inert USP Class VI, ADCF materials, and positioned inside the vessel in the area where the analyte in question is to be measured. The coatings are sometimes referred to as "spots."

Figure 3:
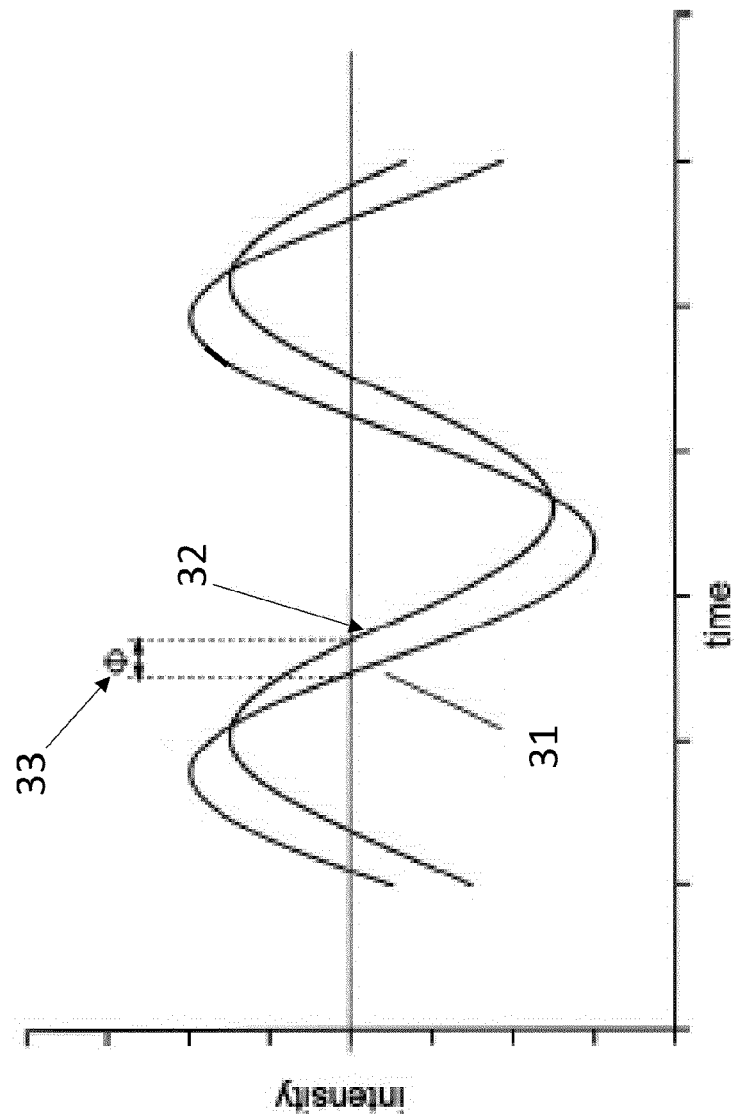
FIG. 3 shows relative phase difference of the excitation and fluorescent signal.

This sensing modality has evolved rapidly over the last 20 years as the telecom revolution provided inexpensive optical sources (LEDs) and detectors. This type of sensing is popular in bio-processing, and more generally in, e.g., medicine and biotechnology as it can be either miniaturized, or made non-invasive, or both. It is also important to note that the sensor elements can and are produced in USP Class VI, animal component derived free (ADCF) formats. With advances in electronics and light sources, the use of information gathering in the frequency domain has become an attractive approach to the art of fluorescent sensing. Sensors that utilize the phase delay of the fluorescence signal relative to the modulated excitation signal are based on fluorescence lifetime. Phase fluorometric systems work by detecting a change in the phase lag of the emitted fluorescent signal as a function of analyte concentration. In most cases, this approach has been found to be a more efficacious basis for a sensor than monitoring the quenching of fluorescent intensity in the time domain. In general, an optical excitation source is modulated at a frequency, f, and the light impinges upon an analyte sensitive dye. The dye re-emits light at a longer wavelength (a fluorescent signal) with the same modulation frequency, but with a delay in phase, as shown in FIG. 3. The phase delay is caused by the fact that the energy levels of the fluorescent material have finite time constants associated with them. In many ways, one can analogize the fluorescent material to a classical electrical low pass filter to understand the origin of the delay. The fluorescent states can be thought of as a capacitor which has a capacitance that is a function of the environment. At a given frequency, the phase of the signal passed by the low pass filter is mediated by the capacitor's value. In a similar way, the phase delay between the excitation signal and the emitted fluorescent signal is a function of the analyte concentration. An example of this delay is represented in FIG. 3. (See C. M. McDonagh et al., *Phase fluorimetric dissolved oxygen sensor*, Sensors and Actuators B 74, (2001) 124-130, incorporated herein by reference in its entirety). FIG. 3 shows the excitation wave 31 and the emitted or fluorescent wave 32 as well as the phase delay, 33, between the two. The relationship describing the phase delay, $\phi$, and its relationship to the modulation frequency, f, and the fluorescent life time $\tau$ can be represented by the following equation:

$$\phi = \text{ArcTan}(2\pi f\tau)$$

where $\tau$ will change as the analyte concentration changes, which means that $\phi$ will also change as the analyte concentration changes. Methods and suitable data processing equipment which allow one to calculate the phase delay between the excitation signal and the fluorescence signal are known to one skilled in the art (Lakowicz, *Principles of Fluorescence of Spectroscopy*, $3^{rd}$ edition, Springer 2006, incorporated herein by reference in its entirety).

Figure 4:
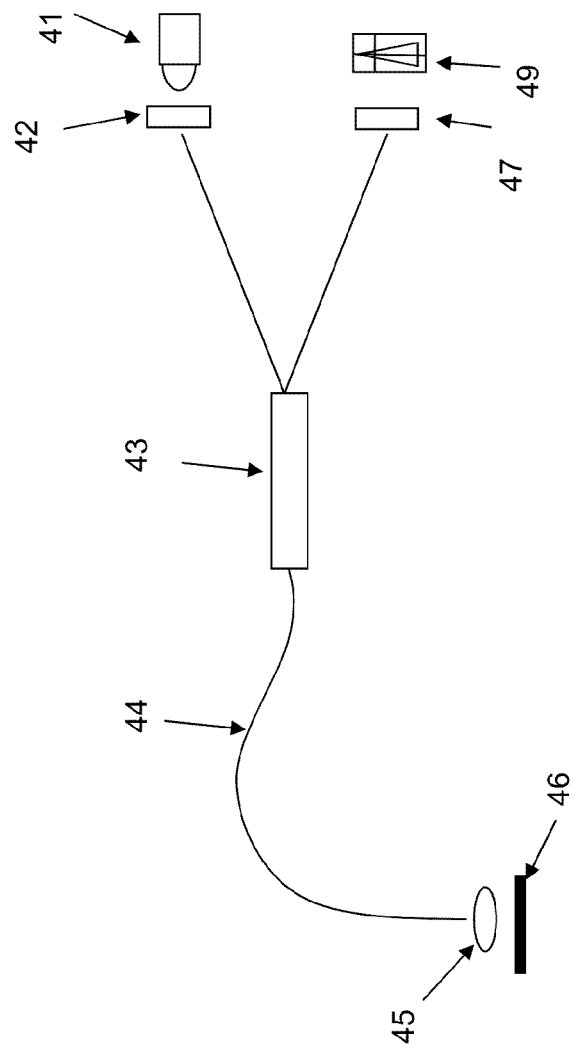
FIG. 4 shows a fiber-optic phase fluorimetry system.

The construction of phase fluorimetric based sensors has generally favored using fiber-optic based illumination and collection geometries, though this is not the only method. A fiber optic based design is shown in FIG. 4. An aspect of the system pictured in FIG. 4 is that the excitation light 41 is remotely filtered by 42 and coupled into a fiber 43, while the collected fluorescent signal from 46 that returns through 44 is delivered through a filter 47 to a photo-detector 49 which is also located remotely from the dye 46 and lens 45. This allows a system where the optical sources and coupling all occur at the same location as the data processing electronics. While this simplifies some of the design and implementation issues and allows the use of fiber-optic for both delivery of the excitation light and collection of the fluorescence signal from a remote location, it is also limiting in several ways. First, the fiber's ability to withstand bending and other mechanical perturbation is limited. Leakage of both illumination light and signal light caused by bending the fiber or fiber bundle results in the excitation light actually impinging on the fluorophore being of lower than optimal power, and loss of the collected fluorescent signal can significantly reduce the signal to noise ratio. The use of multiple fibers or fiber bundles can help, but dramatically increases the cost and complexity of the system. The collection of the fluorescent signal is often the most vexing problem, and the ability of the fiber (or fiber bundle) to collect light is limited so that most systems of this type collect substantially less than 10% of the light emitted by the fluorophore. This usually results in using a much higher intensity excitation beam than required. This is important because the fluorophores are subject to photo-degradation and their useful sensing lifetimes are limited by this fact. The photo-degradation of the fluorophore and even of the host matrix on which the fluorophore is immobilized in is evidenced by drift in the readings and a lower fluorescence efficiency.

Figure 5:
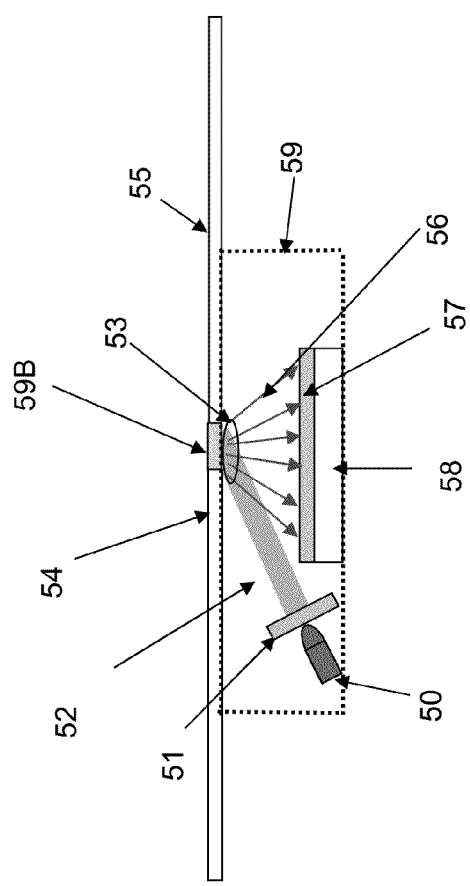
FIG. 5 shows a free space optical phase fluorimetry system.

Because of the issue with photo-degradation, another method of constructing a phase fluorimetric sensor using free space optics has gained market acceptance. Free space optics allows for a large increase in the efficiency of collection of the fluorescence emission light and thereby a large decrease in the excitation light. The decrease in the excitation light allows a corresponding decrease in the rate of photo-degradation and therefore a longer sensing lifetime of the fluorophore. This method is described in U.S. Pat. Nos. 7,489,402 B2 and 7,824,902 B2 and the teachings of these are incorporated herein, in their entireties, by this reference. FIG. 5 shows an example of this type of free space optical phase fluorimetric sensing system. In FIG. 5, element 50 is the excitation source (typically an LED), element 51 is a filter to shape the spectrum of 50. 53 is a lens which helps focus the light 52 onto 59B, the fluorophore. Element 54 can be a single-use element on which the fluorophore 59B is mounted in, or it can be the inner wall 55 of the bioprocess container/bioreactor. The emitted fluorescent signal, 56, is sent through a filter 57 which filters out the light not at the wavelengths (color) of the fluorescent signal before it impinges upon a photo-detector 58. The entire optical assembly is typically enclosed in an opaque housing, 59, which blocks ambient light from both the fluorophore and the detector.

Figure 6:
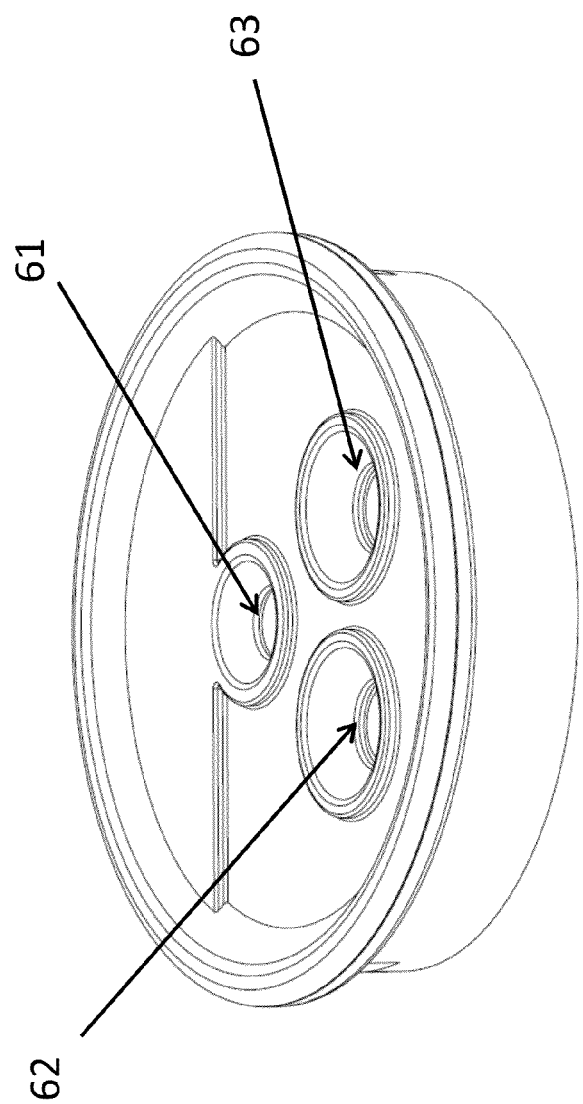
FIG. 6 shows a free space optical carrier.
Figure 7:
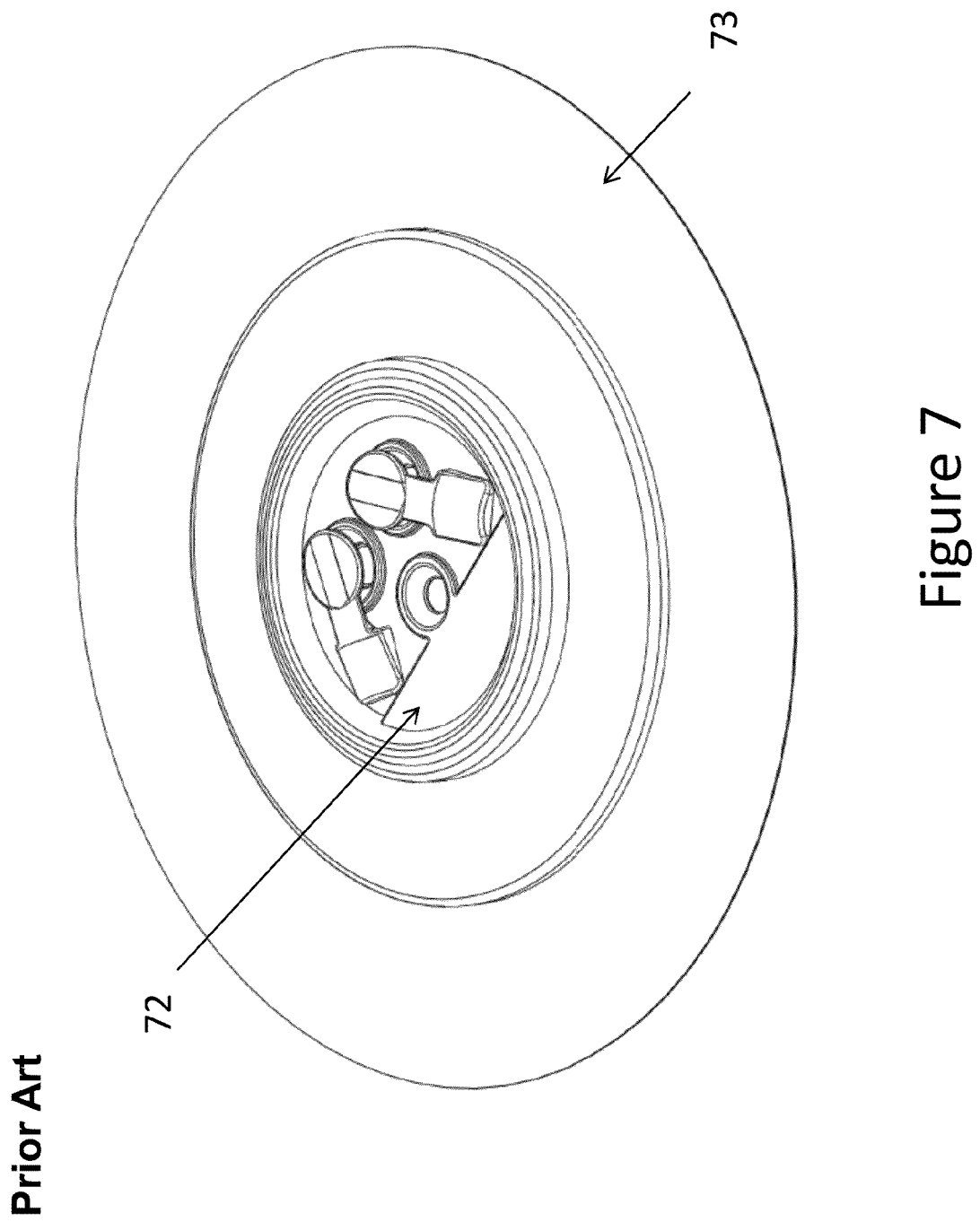
FIG. 7 shows the carrier of FIG. 6 in a mounting flange for use in flexible bio-processing system containers.

FIG. 6 shows the physical platform on which the fluorophore or opto-chemical sensor spot is mounted. Other parameters (e.g. temperature) can be measured through this physical platform or "carrier." The particular carrier shown in FIG. 6 is configured to measure dissolved oxygen and pH through the use of opto-chemical sensor spots mounted in the recessed "cups" 62 and 63 and temperature via cup 61 having a 316L electro-polished plate that is molded into the carrier. FIG. 7 shows this carrier sealingly affixed to a mounting flange. In FIG. 7 the prior art carrier is shown as 72 and the mounting flange is shown as 73. The mounting flange is typically made of some form of low density polyethylene or compatible material so that it can be thermally welded to the inner layer of a flexible bio-process container. This is described in US Patent Application No. 2012/0244609 A1 and the teaching is herein incorporated by reference in its entirety.

All of the phase fluorimetric optical sensors share a common characteristic, which is that the fluorescent dye that enables the sensing must be inside the bioprocessing vessel. As previously noted, persons of skill in this field of bioprocessing have noted that the sensing spots do not work the same after gamma radiation as before gamma radiation. As mentioned, gamma radiation can chain scission the dyes and matrix comprising the sensor spot, as it does all materials. The details of the interaction of the gamma radiation with the materials used to construct single-use bioreactors and their contents were not well understood as evidenced by the paper by Hammond et al. Irrespective of this, some effects have been noted and attempts made to overcome them. This is evidenced by the following series of 3 patents that attempt to address the aforementioned issues. These patent applications are all aimed at methodologies to shelter or isolate the sensor spot from the substances created in the single-use vessels during and immediately following gamma radiation. These patent applications (WO 2010/001457 A1, WO 2011/066901) are aimed at minimizing the volume of the compartment the spot is contained in during the gamma process by creating a type of pocket or housing that shelters the spot. While this minimizes the interaction with some of the volatiles created by the gamma sterilization process, it does not eliminate the effects entirely. The third patent application (WO 2011/015270 A1) focuses on coating the spots with a substance that dissolves when the vessel is filled with liquid (e.g. media for cell growth). The patent teaches uses glycerin or glucose as the coating. There is, however, no clear study showing the degree of protection these coatings offer no evidence that other issues are not created by these coatings during the gamma sterilization process.

Finally, none of these approaches address the fact that the spots themselves are still subject to chain scissioning by the gamma radiation. The chain scissioning of the dye molecules and the host material in which it is embedded (the spot) is evidenced by the fact that the time response of the sensor spot is generally significantly slower and the phase response of the spots altered during the gamma process. The time response for a pH sensor when gamma radiated at 40 kGy can be significantly slower (2× or more) than before gamma radiation, and the phase response is typically altered such that the usable measuring range is significantly reduced. This change in the phase response of the spot also causes the calibration of the spot to be dramatically different than before gamma radiation and therefore can render the spot useless. Given the ambiguity in the dose level inherent in gamma sterilization, it is exceedingly difficult to pre-calibrate the spots. The typical sterilization range is 25 kGy to 40 kGy (with many using 25 kGy to 50 kGy), and the calibration is significantly different between these two extrema dose levels. Clearly one can try to provide a calibration in the middle of the range and hope that this is representative of the gamma dose. Given that most vendors of single-use vessels try to minimize their sterilization costs by loading large pallets with their product and having them sterilized simultaneously in a chamber, the spread across the pallet in the run is often 25 kGy to 40 kGy or more. This means that some of the single-use vessels might receive close to the minimum dose and some close to the maximum and therefore the single-use sensors are required to work across a large range of gamma radiation values. Unfortunately, this is often very difficult if not impossible.

Figure 24:
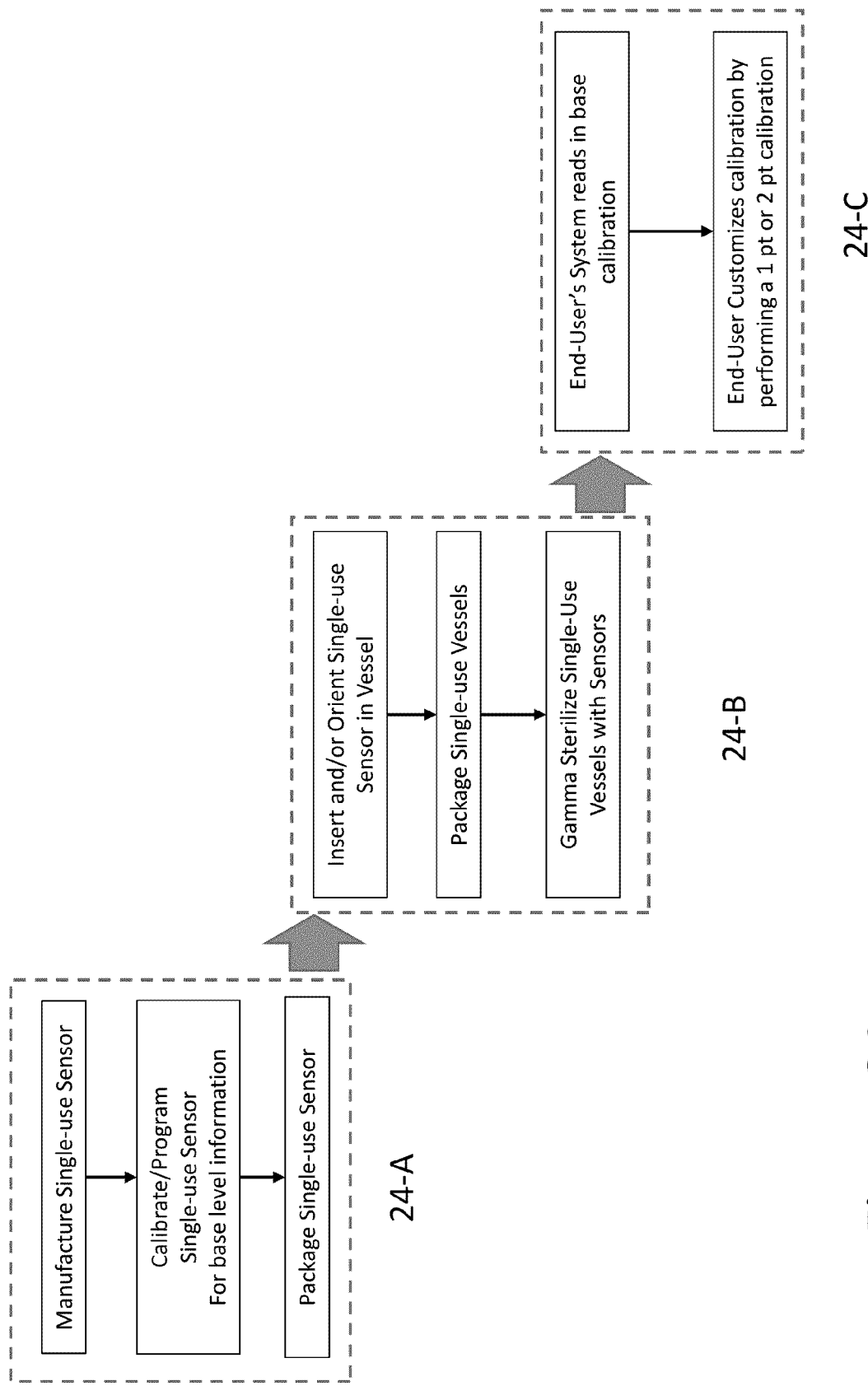
FIG. 24 shows a flow chart of a method currently employed for inserting single-use sensors into single-use bioprocess vessels. It details the construction process, the calibration process, the sterilization process, and the transportation required between parties involved. The parties are the single-use sensor manufacturer, the single-use bioprocess vessel manufacturer, and the end-user.

A current typical process for implementing and using single-use opto-chemical sensors is outlined in the flow chart shown in FIG. 24. In the boxes 24-A, the manufacturing and calibration of the sensor are described; this activity is generally performed in a particulate controlled environment (e.g., a clean room). Typically the opto-chemical sensors (e.g. spots) are produced and either coated onto the surface to be exposed to the analyte or coated onto a material like, but not limited to, polycarbonate and then the spots are punched out of this sheet of material. Either way, some of the sensors, in whatever form is therefore convenient, are calibrated for their use conditions (e.g. sterilization conditions, analyte details), and the calibration is made available by memory chip, barcode, or simple manual data entry. Once the sensor calibration is complete and verified, the sensors are packaged. This packaging is typically optically opaque and often with 2-3 layers of bagging for entry into cGMP receiving, and clean rooms. In the next box, 24-B, the activities which happen at the single-use bioprocessing vessel vendor's location are described. Typically the opto-chemical sensor spots are positioned and/or oriented in the aforementioned vessel. This can be through a port, through sealingly affixing to the vessel, or by simply adhering the opto-chemical sensor to the inner surface. When the single-use bioprocess vessel construction is completed, the vessels are packaged by double or triple bagging for application in end-user cGMP environments and then packaged in placed in boxes. The boxes are stacked on palettes and sent out for gamma radiation. The size of the palettes and the varying density make reliable and consistent radiation dosing difficult despite the fact that frequently many dosimeters are placed around the palette during sterilization. Additionally, spatial hot spots in the dosing are common and often difficult to avoid leading to further variability and ambiguity in the radiation dose the opto-chemical sensors receive. This can lead to decreased accuracy of the calibration now associated with the opto-chemical sensors even under ideal conditions. The box, 24-C, describes the end-user actions once the single-use bioprocess vessel is received. The end-user typically unpacks and sets up the vessel, and then either enters the calibration data by scanning, manual entry, or automated readout (e.g. Finesse Solutions' system). The user then performs a 1 point standardization of the sensor or a 2 point re-calibration (Finesse Solutions' system capability). Generally speaking, the 1 point standardization is not sufficient to allow opto-chemical pH sensors to function well enough for use.

When phase fluorescent sensor chemistry (the spot) is exposed to the gasses or other byproducts created in the single-use vessels during gamma radiation and simultaneously to the gamma radiation itself, the two effects may combine to render the sensor inaccurate or simply not usable. One way to mitigate some of the effects of gamma irradiation is to develop a detailed pre-calibration method and a sophisticated user based calibration scheme. If the conditions in the single-use vessel during the gamma or e-beam sterilization process include significant amounts of water, isopropyl alcohol, air, and/or organic phosphates, the results of the radiation process are sensor spots which are not functional even with intervention provided by the aforementioned sophisticated calibration algorithms. Even if the sensors are shielded somewhat from the larger environment of the vessel, the fluorescence properties of the spots is still often significantly compromised such that they are not reliable or accurate enough for use in the intended application (e.g.: controlling the single-use vessel for cell growth, buffer preparation, etc.).

Figure 8:
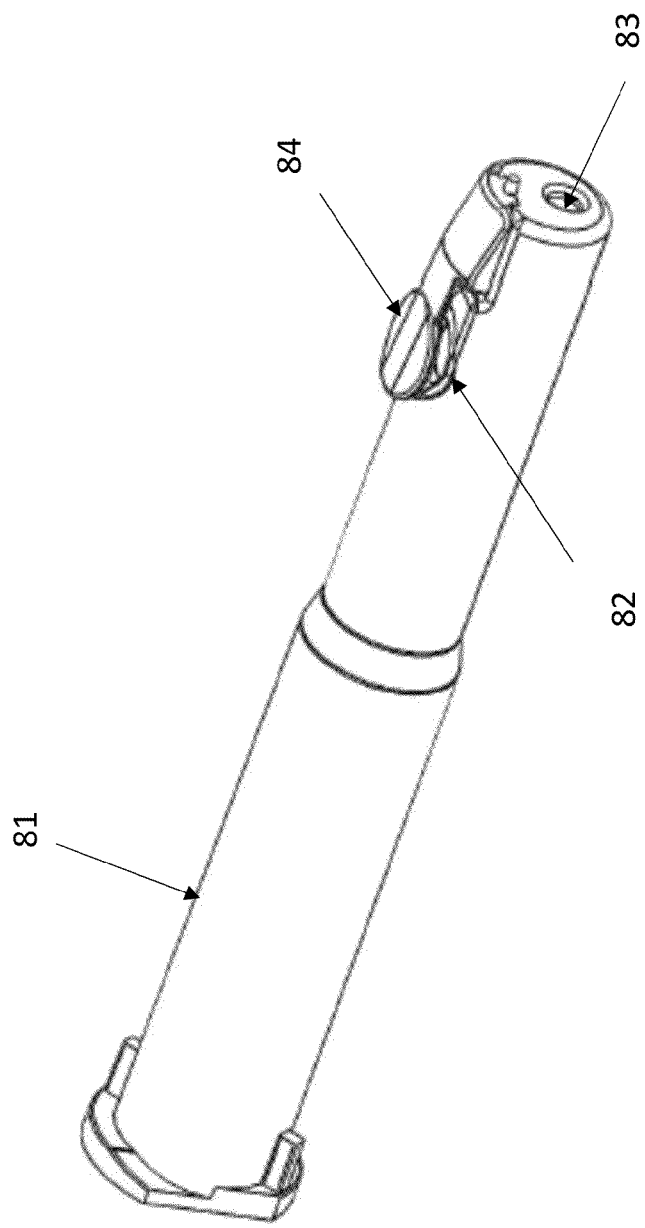
FIG. 8 shows a free space carrier (sheath) used in single-use stirred tanks systems.

One way around this issue is to provide a method and apparatus for separating the sensor spots and the vessels during their respective sterilization periods. Clearly both the sensor and the single-use vessel must be sterilized and the sterility of both the single-use vessel and the sensor spots must be maintained when the sensors are introduced into the single-use vessel. This requirement can be met with an appropriately designed aseptic connector and the appropriate method of handling of the sensor carrier. Here, "carrier"

means the physical element that the sensor elements are mounted on; here "appropriate" means that it is constructed of materials known to not outgas significantly or which can be proven to not outgas significantly during sterilization or other process, including normal end use. These materials include but are not limited to suitable grades (USP Class VI/ISO 1993, animal component derived free, latex free, phthalate free, gamma and e-beam stable) of polycarbonates, polysulfone, Kynar, or co-polyester during either gamma or beta e-beam sterilization and which can be constructed to meet the form factor required for the carrier for the single-use sensor spots. Two such designs are shown in FIGS. 6, 7, and 8. The carriers are meant to work with free space optical systems and they are detailed in US Patent Application No. 2012/0244609 A1 and U.S. Pat. No. 7,824,902 respectively.

Figure 9:
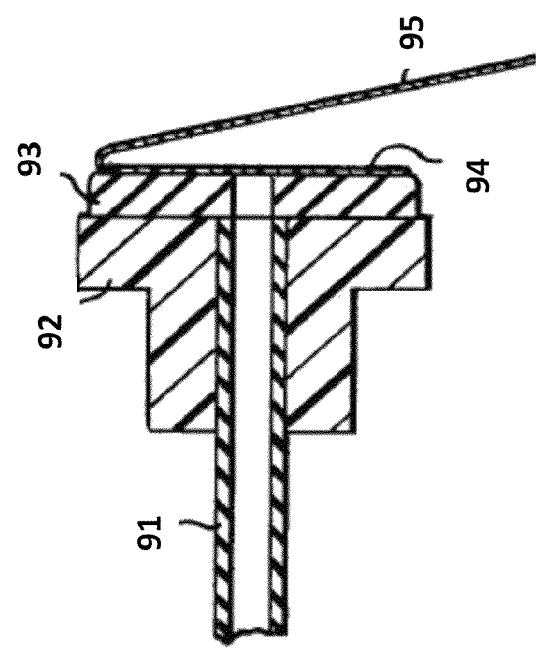
FIG. 9 shows one side of an aseptic connector.
Figure 10:
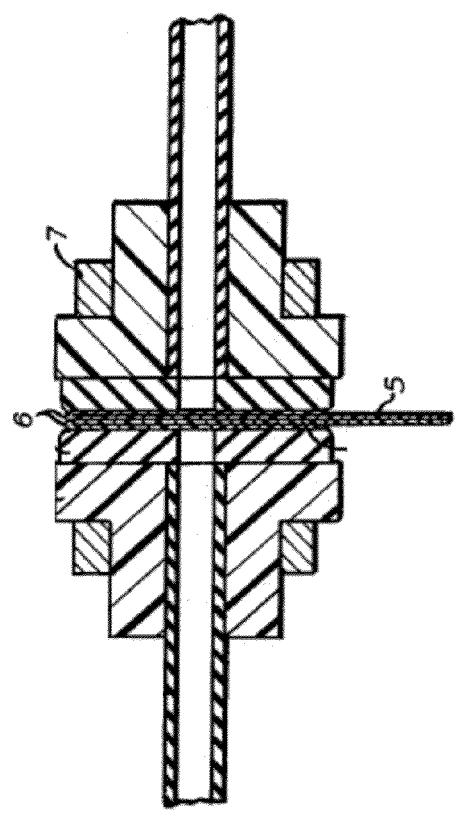
FIG. 10 shows both sides of an aseptic connector system.

Aseptic connectors such as those described in U.S. Pat. No. 3,865,411 (incorporated herein by reference in its entirety) have been used in the bio-processing industry. They have typically been used to make aseptic connections in sets of tubing or anywhere fluid transfer occurs. The basic concepts involve the ability to have two components that can be individually sterilized and maintain their individual sterility before and after being connected. Additionally, when connected they allow for communication between the passageways in the two components. An example from the aforementioned design is shown in FIG. 9. In this figure, 91 is a flexible tube or conduit leading from the receptacle, 92 is an annular flange attached to tubing, 93 is a compressible gasket, 94 is a diaphragm which has a draw tab 95. The conduit 91 must clearly be closed before sterilization and the removable draw tab 95 covers the other opening. Therefore the system can be sterilized and maintain sterility until use. The connectors are used together as shown in FIG. 10. Here the units shown in FIG. 9 are connected and their respective diaphragms 6 are brought together and the tabs 5 are brought together. As described in U.S. Pat. No. 3,865,411, "The assembly of the two fittings is then clamped together by an appropriate mechanical means 7, i.e.: a spring-loaded clamp or a snap-fitting ball, so that the two gaskets are compressed against each with a predetermined amount of pressure to form a tight seal." In practical use, any such implementation that maintains a sterile barrier after the sterilization process can be readily employed in this arena.

This concept of an aseptic connection may be applied to the problem described here. The separation of the opto-chemical sensor spots and the single-use bio-process vessel allows the single-use vessel to be gamma radiated (or more generally stated—sterilized) according to whatever standards are required to meet ISO 11137-2 and the end-users' sterility requirements. It also allows the opto-chemical sensors to be separately sterilized such that they are not exposed to the contents of the vessel during the sterilization process. Additionally, it allows for the decision of which sensors and how many of each to be used in a process to be decided just prior to the run as opposed to months or years before when the single-use vessel is designed and built.

Figure 13:
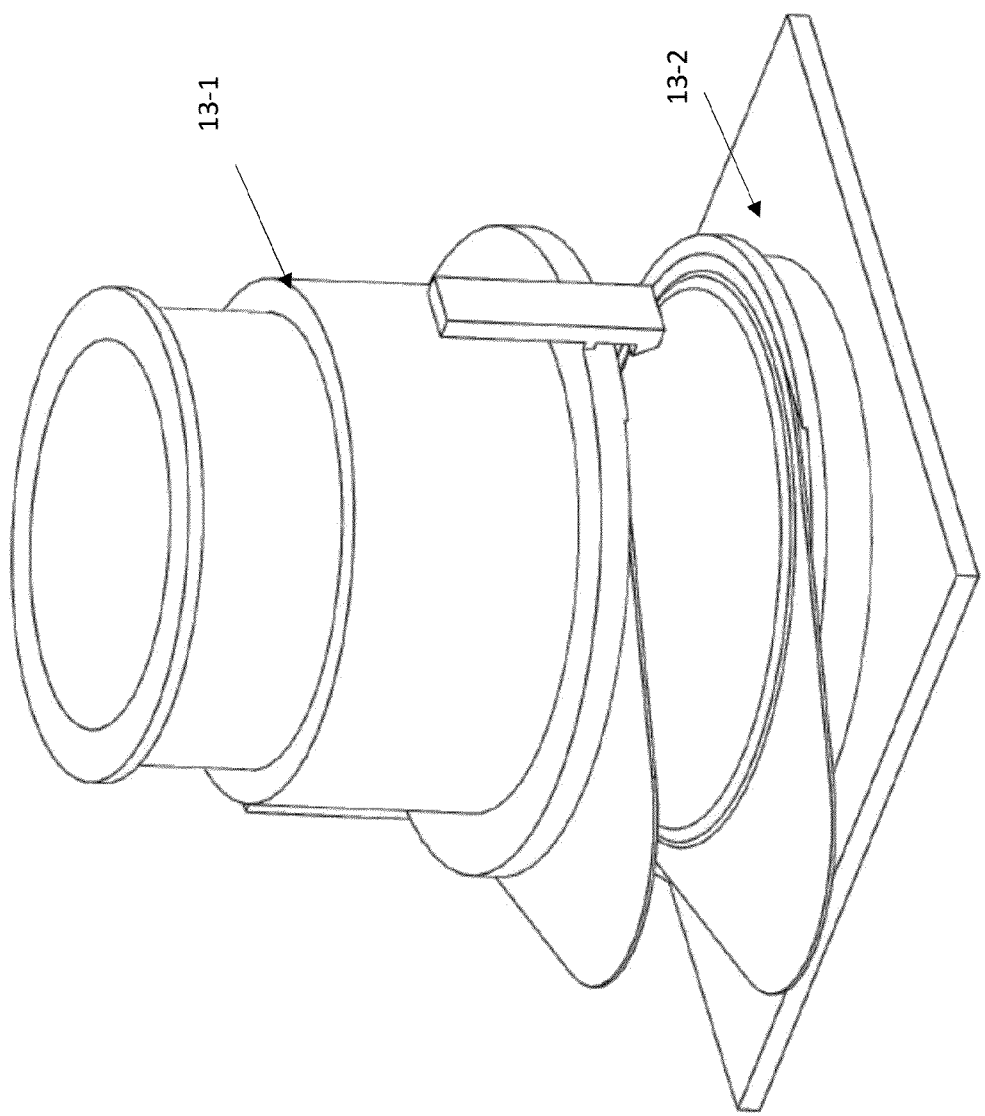
FIG. 13 shows both halves of an aseptic sensor connection assembly prior to connecting them.

An aseptic connector that can be used for this purpose is shown in FIG. 13. The opto-chemical or optical sensor spot and its carrier 13-1 are held in the top section, while the bottom section sleeve 13-2 is attached to the single-use bio-processing vessel (not shown). The sensor may be configured or designed to detect an optical response. In some embodiments, an electrochemical sensor, temperature sensor, pH sensor, oxygen sensor, or single use sensor is held in the carrier 13-1. In some embodiments, two or more sensors are held in the carrier 13-1. In various embodiments, an oxygen sensor, pH sensor, and temperature sensor are held in carrier 13-1. If this were a flexible bag it would typically be thermally welded to the inside surface, but clearly can be attached to any surface of a container through use of welding or suitable adhesives or retention/attachment processes. In a conventional approach, if this were to be welded to a flexible single-use bio-processing vessel, the material on the base of sleeve 13-2 would either have to be compatible with the inner layer of the bag or sealingly affixed to a flange made of such a material. The carrier 13-1 may be disk shaped with the sensor having an exposed sensing surface on the flat side of the carrier 13-1. As described below, in some embodiments, the carrier may be generally sheath shaped with the sensor having an exposed sensing surface on an end of the carrier. In some embodiments, two or more sensors in carrier 13-1 have exposed sensing surfaces on a flat side of the carrier 13-1.

Figure 14:
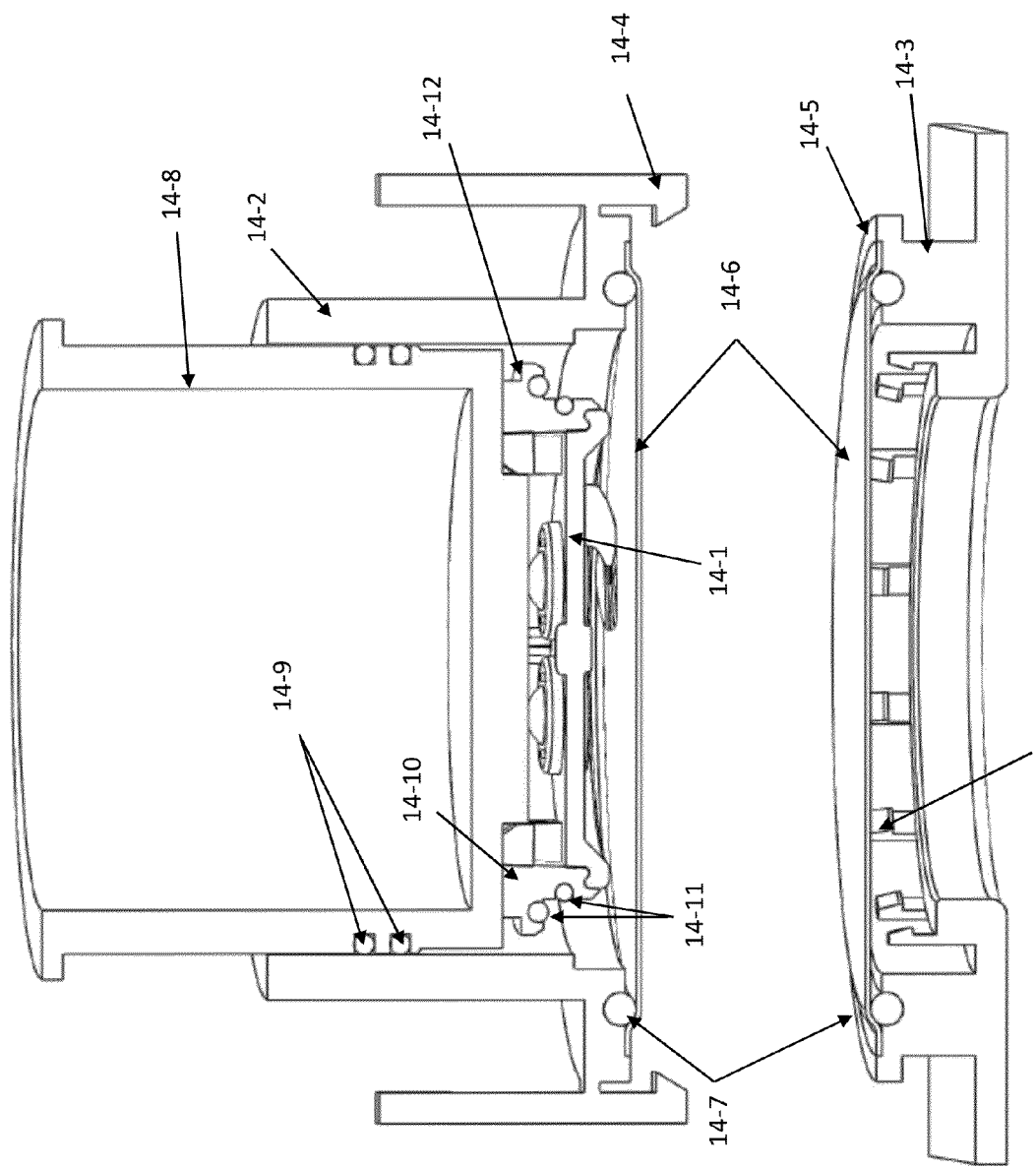
FIG. 14 shows the detailed cross-sectional view of the sensor connector assembly shown in FIG. 13.

While the following examples show sensor-containing assemblies, this disclosure is not limited to sensors. Other peripherals such as filter flow tubes, sample ports, etc. may be used in place of sensors in the following examples. FIG. 14 shows an aseptic sensor connection assembly for installing a sterilized sensor in a bio-processing vessel via an aseptic vessel connector or aseptic connector 14-3 affixed to the vessel. The Figure depicts a full cross-sectional view of both halves of the aseptic sensor connection assembly prior to the connection being made. Shown is an example of an optical carrier 13-1 as shown in FIG. 6. Here the carrier depicted in FIG. 13 as 13-1 is labeled as 14-1 and as before, holds the opto-chemical sensors spots and the stainless steel window for temperature sensing.

The sleeve 14-2 is a substantially tubular part of the top portion of the aseptic connector that encloses the carrier 14-1 and its sealing flange 14-10; this entire assembly holding the sensor will be referred to as the sensor applicator or applicator, having an applicator connector 14-4. The applicator may be composed of a polycarbonate, polysulfone, polyvinylidene fluoride, co-polyester, or a combination of any of these. The sleeve 14-2 may be constructed of rigid material. The applicator may be configured to be removed from the carrier 14-1 and the bio-processing vessel after the carrier is installed in the bio-processing vessel. The lower half or aseptic connector 14-3 is attached to the single-use bio-processing vessel so that the sensor carrier 14-1 can be aseptically connected to the vessel at a later date and processed independently and will be referred to as the aseptic vessel connector or aseptic connector 14-3. The two halves are sterilized independently prior to the time when they are connected. It should be noted that the parts are all required to be made of gamma, beta, or x-ray stable materials and that all wetted materials will be required to meet ISO 10993/USP Class VI, requirements as well as be animal component derived free, latex free, and phthalate free. The applicator connector 14-4 is configured to temporarily connect to the aseptic vessel connector 14-3. The applicator connector 14-4 may be a clip or retaining device which, when the two components (applicator and aseptic vessel connector 14-3), are united by compressing o-rings 14-7, can latch around the ledge or sealing member 14-5 thereby forming a hermetically sealed unit. While the applicator connector 14-4 is depicted as a clip or latch here, any mechanical device element that allows the o-rings or equivalent sealing devices to be engaged and locked together can be utilized such that the applicator connector 14-4 is configured to provide a hermetic seal with the aseptic vessel connector 14-3 while the plunger 14-8 inserts the carrier 14-1 into the aseptic vessel connector 14-3. In some embodiments, the applicator connector 14-4 is an o-ring.

Once the two halves are hermetically locked together, the temporary removable hermetic sealing tabs 14-6 are removed, simultaneously allowing an opening between the two halves. Prior to being removed, the removable hermetic sealing tabs 14-6 cover a vessel-facing opening of the sleeve 14-2 to maintain the sterilized sensor in aseptic condition prior to installing the sensor in the bio-processing vessel. The hermetic sealing tabs 14-6 may be configured to be removed from the aseptic sensor connection assembly after connecting the applicator to the aseptic vessel connector 14-3 on the bio-processing vessel at a location where the sterilized sensor is to be installed, and before plunging the carrier 14-1 from a position within the sleeve 14-2 to a position engaged with the aseptic vessel connector 14-3. These tabs can be made of a simple film for low pressure situations, or can comprise a USP Class VI, latex free, phthalate free, ADC plate. The tabs can be coated with an adhesive to allow them to stick together (or any other technique can be employed that allow the surfaces of the tabs to naturally bond) to facilitate their simultaneous removal.

The opening allows the depression of the plunger 14-8 through 14-2 pushing the O-rings 14-11 of the carrier/flange 14-1/14-10 into the body of aseptic vessel connector 14-3. The plunger 14-8 may include the O-rings 14-11 to form the hermetic seal while the plunging occurs. As these O-rings 14-11 are compressed forming a hermetic seal, the retaining clips 14-13 latch around the ledge or sealing member 14-12 holding carrier 14-1 into aseptic vessel connector 14-3. The sealing member 14-12 is configured to form a leak-tight seal with the aseptic connector 14-3 where the carrier 14-1 is installed. As mentioned above, O-rings 14-11 provide for a hermetic seal as a sealing member 14-12, but any similar means (e.g. gasket, clip, etc.) can be utilized for this purpose. It should also be noted that the O-rings 14-9 maintain a hermetic seal between sleeve 14-2 and plunger 14-8 through the sterilization process and as plunger 14-8 is depressed. The preferred embodiment of the hermetic seal will be maintained without the use of a lubricant or similar material, as minimizing the amount of materials that can be wetted minimizes the risk of any contamination. However, USP Class VI/ISO10993, animal component derived free, latex free, phthalate free materials do exist and can be used to enhance or enable a hermetic seal. For example, silicone products like the materials offered by NuSil (nusil.com/Products/Healthcare/Restricted/Documents/Restricted%20Healthcare%20Materials%20Selection%20Guide.pdf). Clearly using this aseptic connector 14-3, there is no need for a port or other coupling method to introduce the optical carrier of FIG. 6 or similarly purposed opto-chemical sensor mounting plate into a single-use bio-processing vessel.

Figure 15:
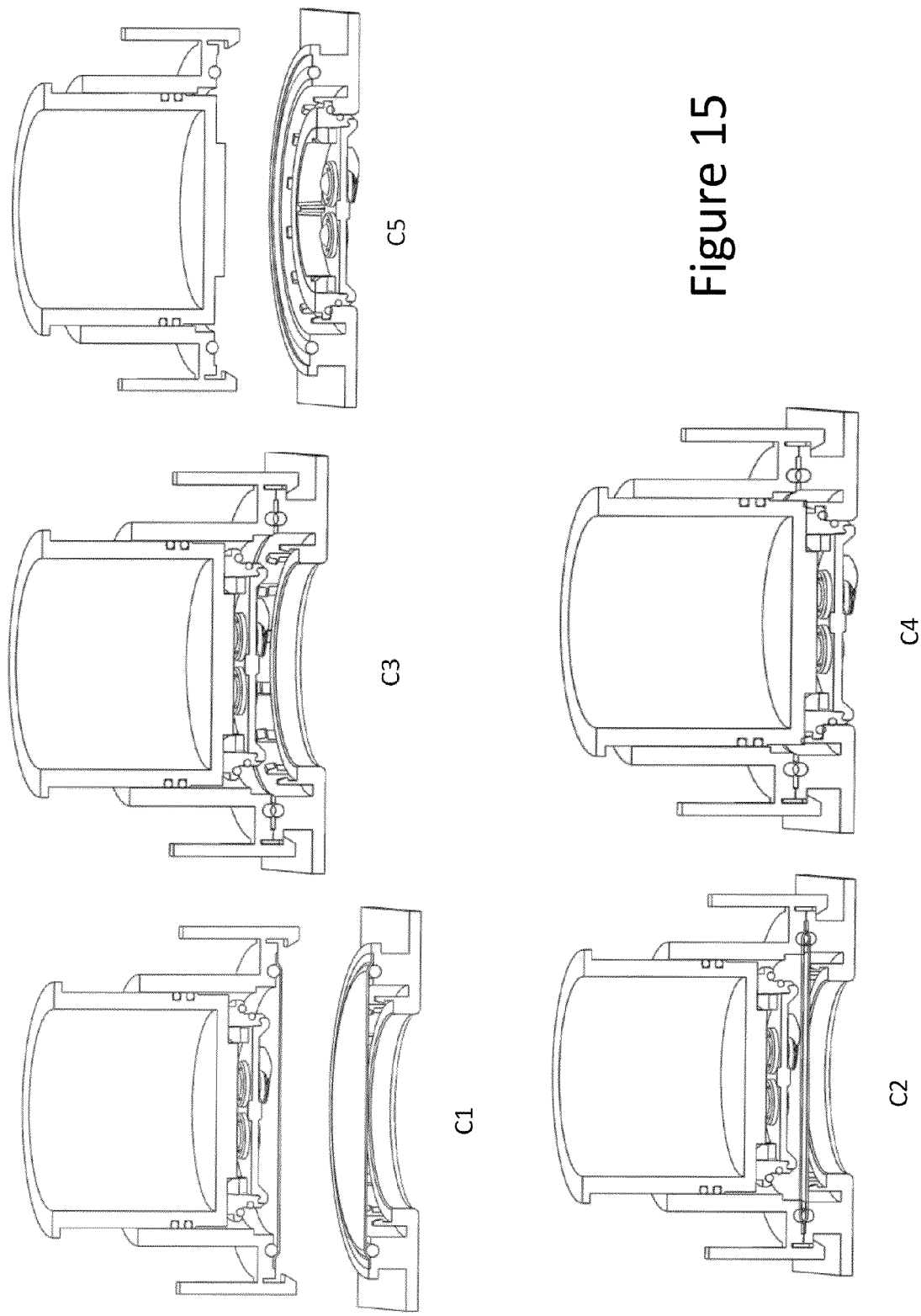
FIG. 15 shows the step-by-step deployment of the aseptic sensor connector assembly.

The process of attaching and deploying the connecting of the applicator and aseptic vessel connector are shown in FIG. 15 where C1 shows the pre-sterilized separate parts. C2 shows the two parts connected and locked together. C3 shows the locked parts with the removable hermetic sealing tabs removed so that there is communication between the two halves of the assembly and therefore between the single-use bio-processing vessel and the optical sensor carrier. C4 shows the plunger depressed and the carrier locked into place in the vessel-mounted portion of the aseptic vessel connector. C5 shows the entire detached plunger, and applicator where the carrier used to be, and the optical carrier and sensors deployed in the vessel, leaving the sensor ready to use.

In certain embodiments, the single-use bio-processing vessel will not be filled with fluid or used in such a manner here that is a large (greater than approximately 1 psig) pressure internally. A non-functioning carrier or blank can be constructed that can be utilized instead of the optical carrier with active elements. This blank would be employed to seal the aseptic vessel connector so that the vessel can be filled with liquid without the potential for leakage around the aforementioned removable hermetic sealing tab.

This concept can be used with other forms of carriers, including the optical sensor carrier shown in FIG. 8. In FIG. 8, the cylindrical body of a sheath-type carrier, 81, is opaque, and there is an optically transparent lens or window 82 on which the opto-chemical sensor spot is glued or deposited. An optional light shield 84 is used for spots that cannot support an opaque coating. Additionally, a stainless steel plate 83 is molded in and acts as a thermal window through which temperature can be sensed. Of course, other sensor configurations can be used in sheath-type carriers.

Figure 16:
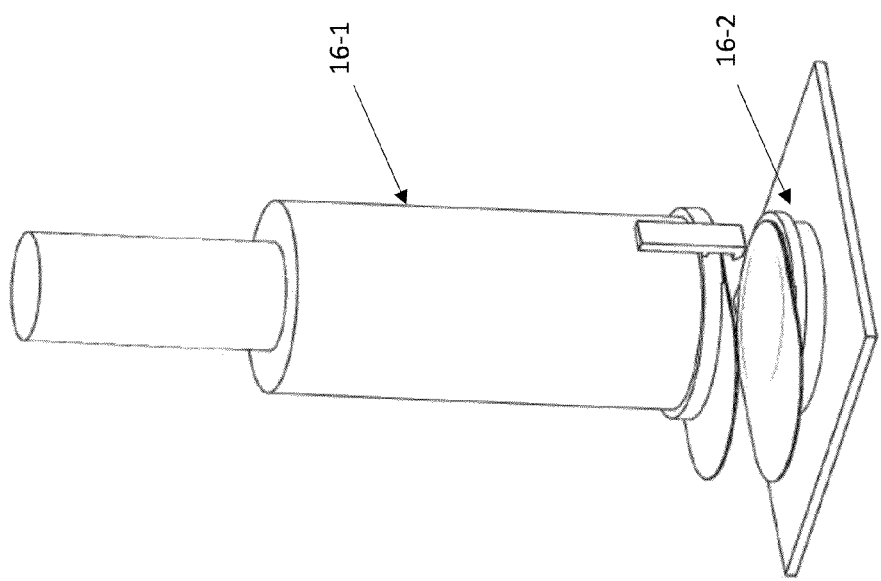
FIG. 16 shows both sides of a sheath based sensor aseptic connector system.

FIG. 16 shows a sheath-shaped carrier utilizing a similar aseptic sensor connection assembly as described above, thereby negating the need for a port as shown in FIG. 2. Carrier 16-1 of the applicator (referred to above as the "sensor applicator") holds the sensor, while aseptic vessel connector 16-2 is sealingly affixed to the single-use bioprocessing vessel.

Figure 17:
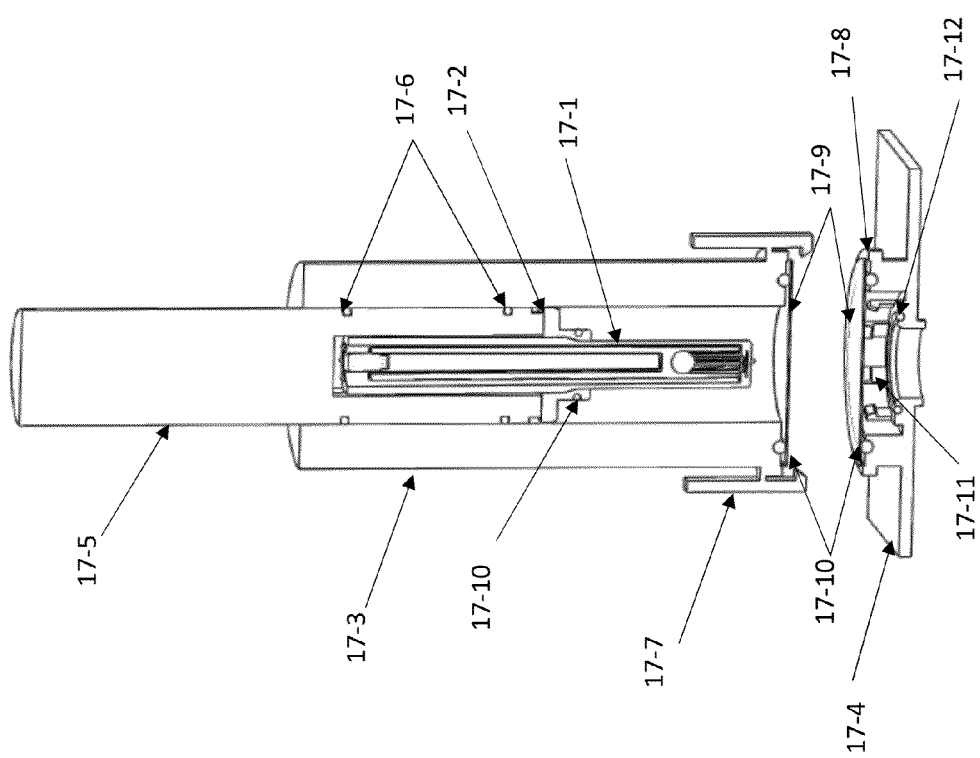
FIG. 17 shows the detailed cross-sectional view of the sheath based sensor aseptic connector system of FIG. 16.

FIG. 17 shows a full cross-sectional view of the sheath-shaped optical carrier as it is adapted for use in an aseptic sensor connection assembly. The aseptic sensor connection assembly here includes a sheath-shaped carrier 17-1 and has a sealing flange or sleeve 17-2, a plunger 17-5, all of which is housed in an applicator 17-3 having an applicator connector 17-7. The sleeve 17-2 is affixed to carrier 17-1 such that there is no leakage around the seal (e.g., leak-tight seal). This seal can be carried out with epoxy or similar method, or it can be designed into the mold of the sheath style optical carrier 17-1 so that the entire aseptic sensor connection assembly is one piece (monolithic).

In use, the carrier 17-1 and sleeve 17-2 are inserted into sensor applicator 17-3, while the bottom half 17-4 of aseptic vessel connector 17-8 is sealingly affixed to the single-use bio-processing vessel as discussed above. These operations may be performed at different times and/or by different entities. The openings to applicator 17-3 are hermetically sealed by the plunger 17-5 and its O-rings 17-6 on the top and by one of the removable hermetic sealing tabs 17-9. The top half of the applicator 17-3 is connected to the aseptic vessel connector 17-8 such that the locking mechanism 17-11 engages with the applicator connector 17-7 allowing the O-rings 17-10 to form a hermetic seal pushing the removable hermetic sealing tabs 17-9 together. The removable hermetic sealing tabs 17-9 are removed, providing an opening between the two halves of the assembly. The comments for the utilization of alternative locking mechanism, the removable hermetic sealing tabs, and the seals mentioned in association with FIG. 14 apply equally here. The plunger 17-5 is depressed pushing the sensor optical carrier 17-1 and sleeve 17-2 into the bio-processing vessel through aseptic vessel connector 17-8 and allowing the locking mechanisms 17-11 to retain the ridge on the sleeve 17-2. The hermetic seal is maintained by O-rings 17-10 and 17-12. With the optical carrier locked in to the aseptic vessel connector 17-8 on the single-use bio-processing vessel, the top half applicator 17-3 and the plunger 17-5 can be removed by depressing or pinching the locking mechanism on the applicator connector 17-7.

In some cases, the peripheral connection assembly may need to be modified from the structure shown in FIGS. 14-17 to accommodate the size and shape of the peripheral. Further, some peripherals will require a custom carrier that is neither a disk nor a sheath.

Figure 18:
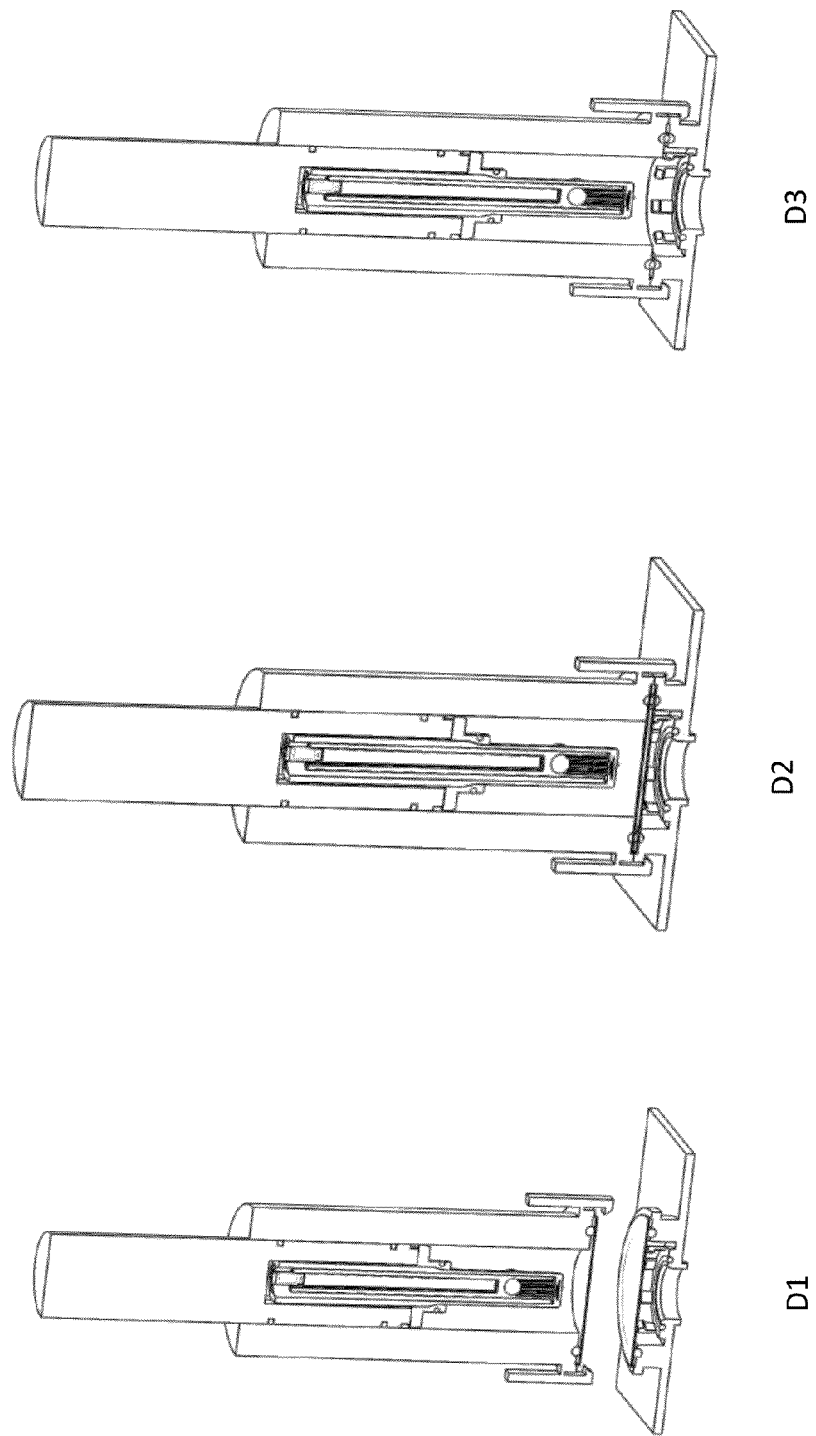
FIG. 18 shows the first three steps in the deployment of the sheath based sensor aseptic connector system.

An overview of this process is shown in FIG. 18 and FIG. 19. In FIG. 18, D1 shows the top part of the aseptic container with the optical sensor carrier contained inside and sealed and the bottom half which would be attached to a vessel. Both halves have been sterilized. D2 shows the two halves connected with the sealing tabs still in place. D3 shows the system with the sealing tabs removed allowing communication between the two halves. In FIG. 19, D4 shows the plunger depressed and the optical carrier pushed through the vessel side connector with the flange locked into place. Finally D5 shows the optical carrier side connector and plunger removed leaving the system ready to use. Again, it should be noted that though it is not necessary, the aseptic connector system shown here may be used before the single-use bioprocessing vessel is filled with any liquid or under pressure. With careful design of the sealing tabs and how they are retained, higher pressures can be accommodated.

Figure 20:
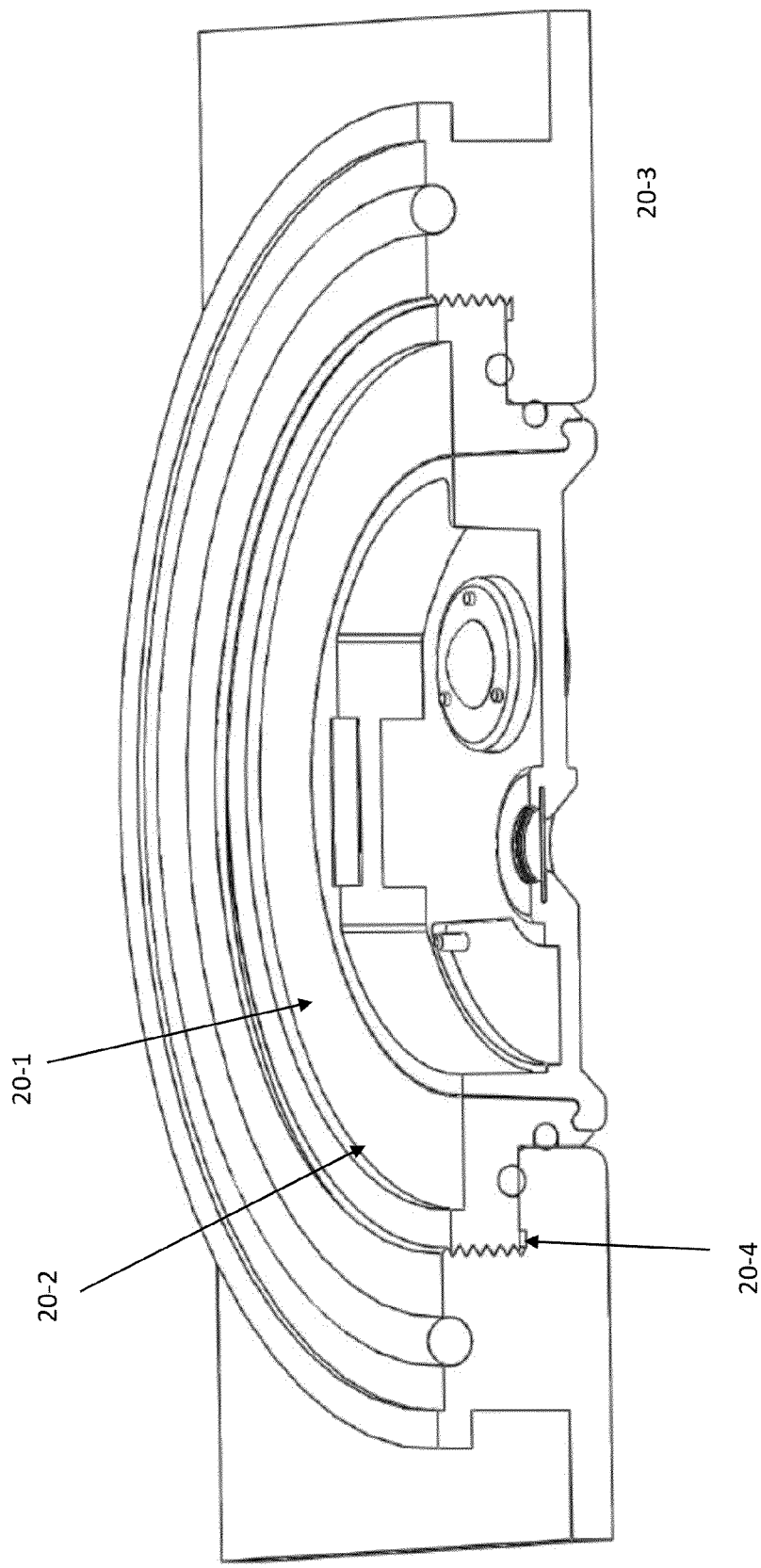
FIG. 20 shows an alternative method of capturing the sensor carrier and flange in the aseptic vessel connector using threads.

As mentioned above, there are a multitude of ways to create an aseptic connection between the carrier/flange and the aseptic vessel connector. FIG. 20 shows a method where the retaining clips in FIG. 14 (14-13) have been replaced with a set of threads 20-4. The sensor carrier and flange assembly 20-1/20-2 are held into the aseptic vessel connector 20-3 by threading or screwing the components together. The plunger (not shown) in this case would be used to screw 20-1/20-2 into 20-3. Care needs to be taken with the materials so post sterilization dimensions still allow for a hermetic seal to be created by the threaded components. A USP Class VI/IS10993 animal component derived free, latex free, phthalate free gel or adhesive can also be applied to the threads 20-4 during construction of the parts and prior to mating of the parts to enhance the hermeticity of the seal. In this system, o-rings are the primary method used to ensure the sealing, but can also be replaced with gaskets or alternative methods of creating a seal between surfaces.

Figure 21:
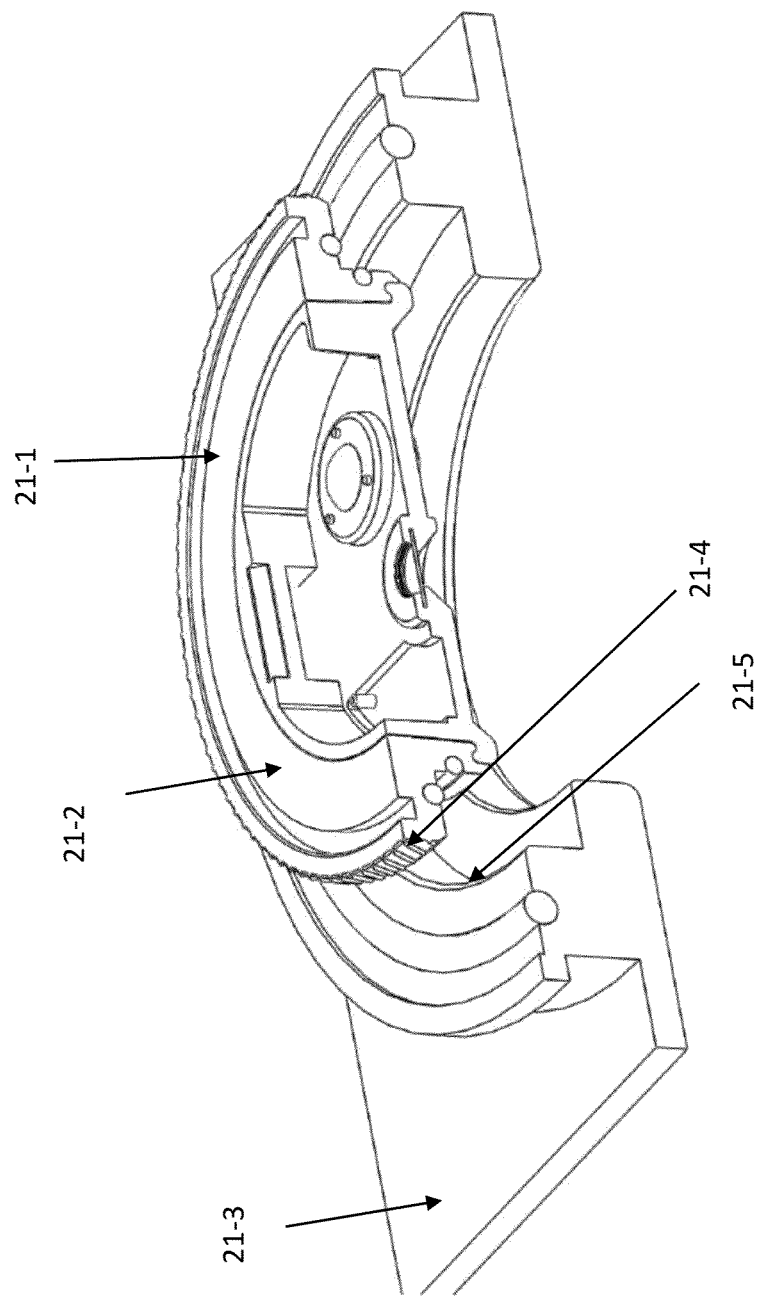
FIG. 21 shows an alternative method of capturing the sensor carrier and flange in the aseptic vessel connector using a press fit.

In FIG. 21 another variation of the connection method is shown where the sensor carrier and sealing flange 21-1/21-2 are shown connected and with a textured edge 21-4. This edge is press fit into the edge 21-5 on the aseptic vessel connector 21-3 and retains the sensor carrier and flange 21-1/21-2 in the aseptic vessel connector. As with the previous methods of making a seal between the sensor carrier and flange 21-1/21-2, the aseptic vessel connector o-rings are shown here but other methods can be employed.

Figure 22:
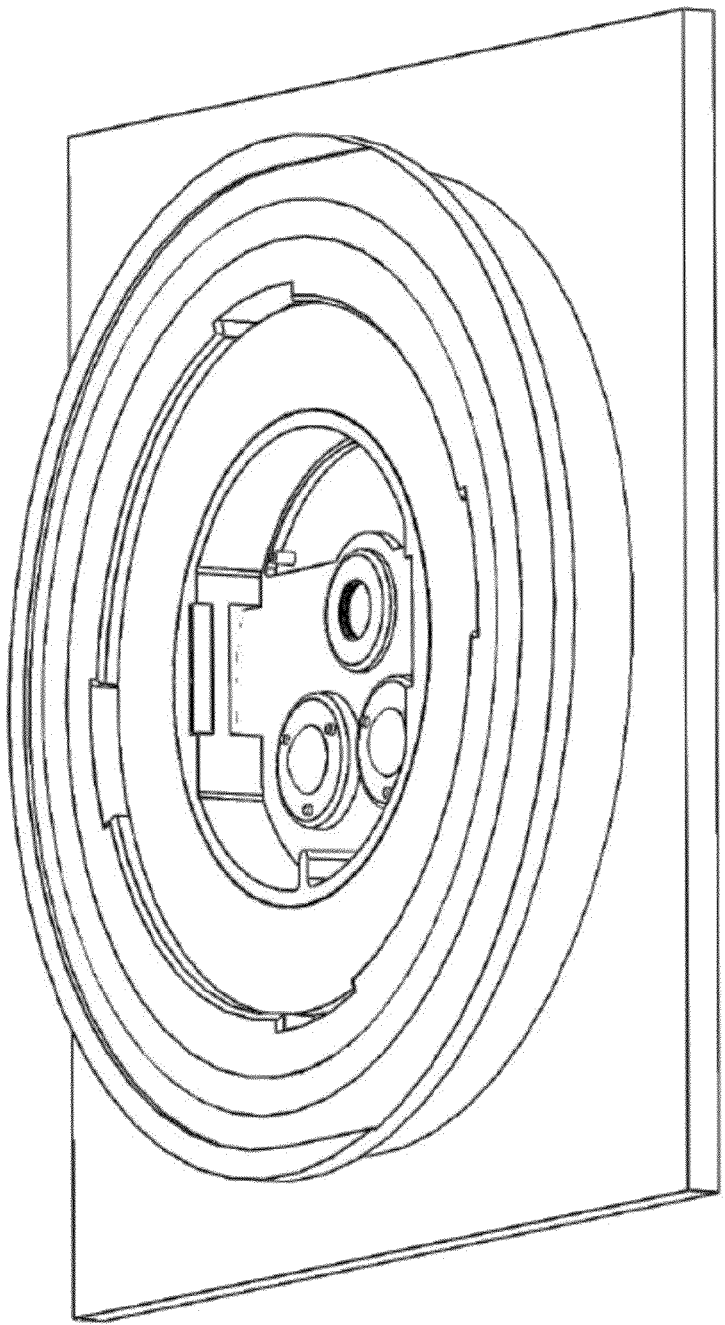
FIG. 22 shows an alternative method of capturing the sensor carrier and flange in aseptic vessel connector using a bayonet mount.
Figure 23:
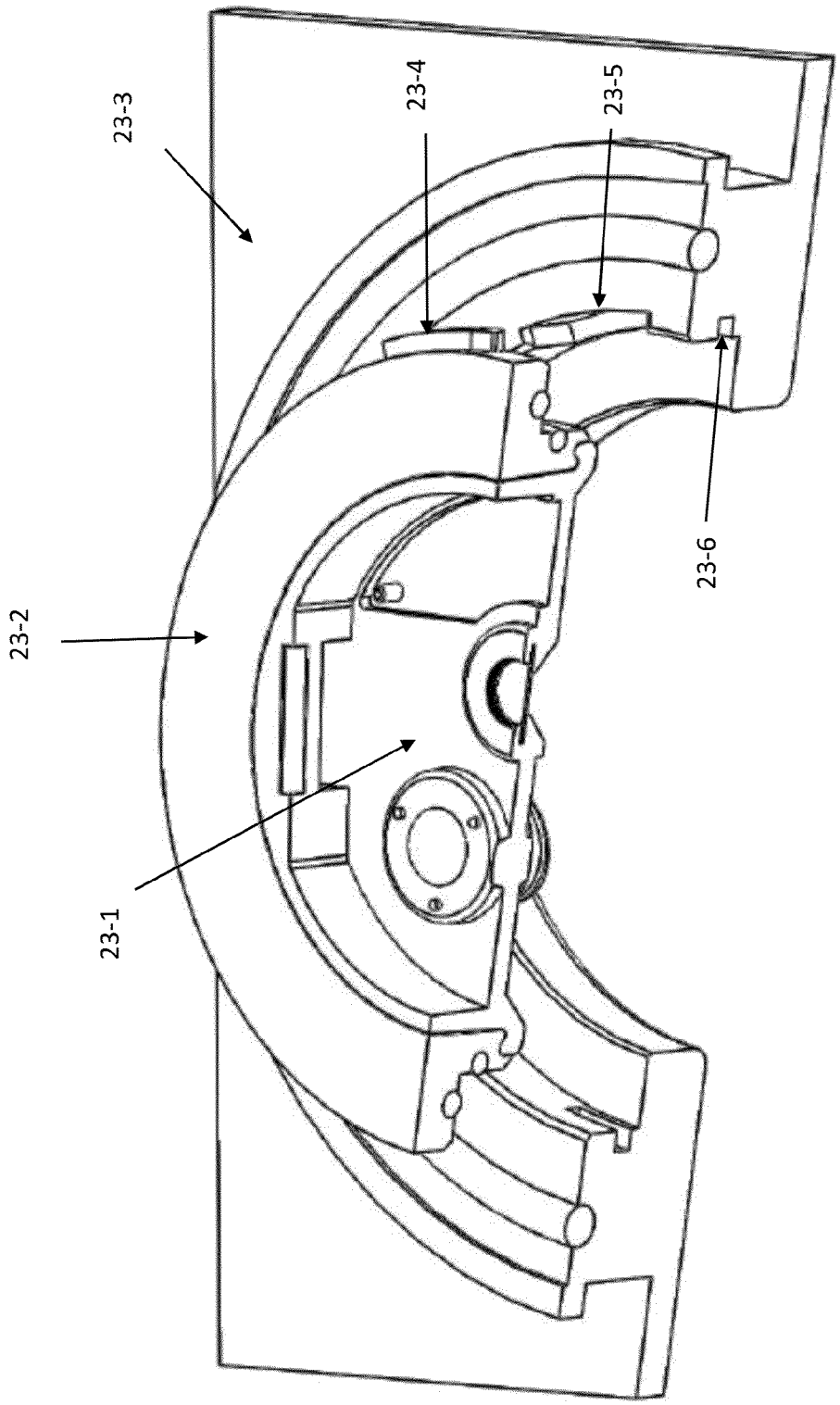
FIG. 23 shows a cross-sectional view of components of an assembly before the sensor carrier assembly is retained in the aseptic vessel connector assembly.

In FIG. 22 a bayonet mounting method of retaining the sensor carrier and flange into the aseptic vessel connector is similar to what is used in many cameras with changeable lenses. In FIG. 22 the system with the connection made is shown. FIG. 23 shows a cross-sectional view of the components before the sensor carrier/flange (23-1/23-2) assembly is retained in the aseptic vessel connector assembly 23-3. The flange 23-2 has mounting segments 23-4 which are inserted into the openings 23-5 in the aseptic vessel connector. The flange with the mounting segment would be rotated clockwise as seen in FIG. 23 such that the mounting segment 23-4 is retained in the groove 23-6. There can be several such segments and grooves around the perimeter of the flange and aseptic vessel connector respectively. The mounting segments will be friction fit into the groove such that the sensor carrier and flange are retained in the aseptic vessel connector with the o-rings maintain the seal as described before.

Other variations on this design can be considered including, but not limited to a retaining clips, a continuously retaining clip etc.

Above a system of separating the sensors and sensor carrier from the single-use bioprocessing vessel has been detailed. In this case the single-use vessel can be gamma sterilized exactly as before without such an aseptic vessel connector attached. If the carrier side aseptic connector is constructed using truly inert materials as described before and the assembly is subjected to gamma radiation in a bag or container constructed of equally inert materials without liquids present, the assembly can be gamma radiated with minimized effect. Specifically, there should be very few free radicals, hydrogen peroxide, organic phosphates or other substances which can affect the performance of the opto-chemical sensor spots. However, there is still the effect of gamma radiation and its potential to compromise the performance of the sensor spots.

While ISO 11137 describes the requirements to minimize colony forming units (CFU) of bacteria and adventitious agents with gamma radiation, the end goal is simply the reduction in the number of CFU's. Several method of implementing the testing are stipulated in ISO 11137-2 including the number of samples to be tested and how they are to be prepared, and further testing if there are failures based on the given criteria.

Figure 11:
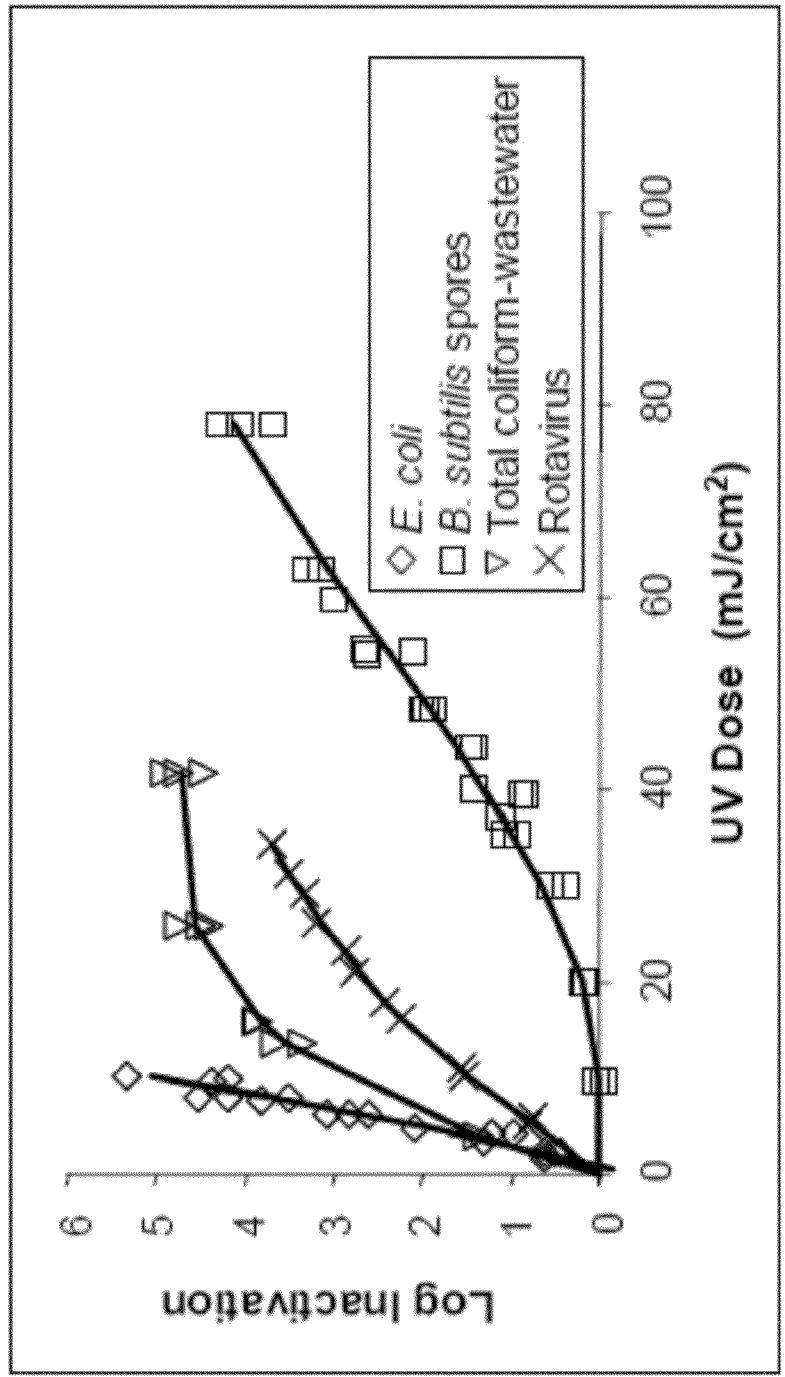
FIG. 11 shows inactivation rates for bacteria as a function of UV dosage.

We describe here a method for minimizing the required level of gamma radiation, beta radiation, or x-ray radiation required to give the same reduction in CFU's. It has been well documented for the treatment of waste water, hospital maintenance, and general surface disinfection, that ultra-violet (UV) light is very effective at reducing the number of CFUs of bacteria and spores. For example, the US Environmental Protection Agency has issued EPA 815-R-06-007, *Ultraviolet Disinfection Guidance Manual for the Final Long Term* 2 *Enhanced Surface Water Treatment Rule*, which is incorporated herein by reference in its entirety. FIG. 11 shows a chart from the aforementioned reference giving dosages in fluence (energy per unit area) required for the log reduction in various types of unwanted bacteria etc. Additionally, the guidance details that the optimal wavelengths of the radiation are between approximately 235 nm and 290 nm with a peak effectiveness around 265 nm. This fluence and wavelength can be provided by pulsed UV lamps as described in the guidance, and by newer technologies such as UV LEDs (e.g. s-et.com).

Figure 12:
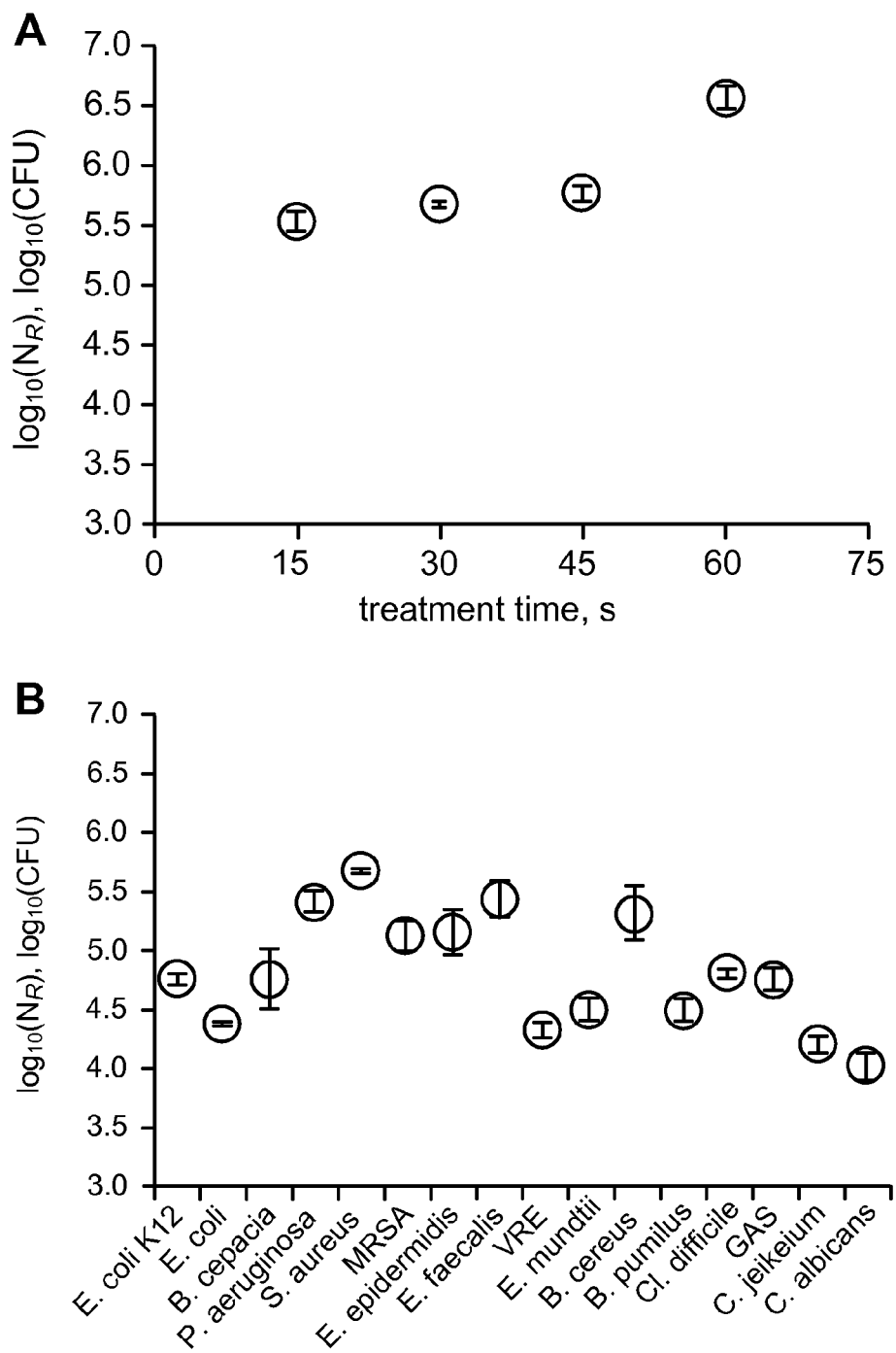
FIG. 12 shows reduction in CFU levels as a function of exposure to cold atmospheric plasma treatment.

Another method for disinfecting and sterilizing is atmospheric plasma based sterilization. A recent publication, "Cold Atmospheric Air Plasma Sterilization against Spores and Other Microorganisms of Clinical Interest", Klampfl et al., Applied and Environmental Microbiology, 78, 15 p. 5077, August 2012, which is incorporated herein by reference in its entirety, describes a study that showed a substantial reduction in CFU's of both Gram-negative and Gram-positive bacteria as well as types of fungus after exposure of samples to a cold atmospheric plasma (CAP). This means that the plasma was created using air at essentially room temperature (under 40° C.); specifically not at high temperature (120° C.) and not with toxic gases like formaldehyde or ethylene oxide. FIG. 12, take from this reference shows the log reduction in various strains of bacteria and fungus created by 60 seconds or less of exposure to CAP.

Figure 25:
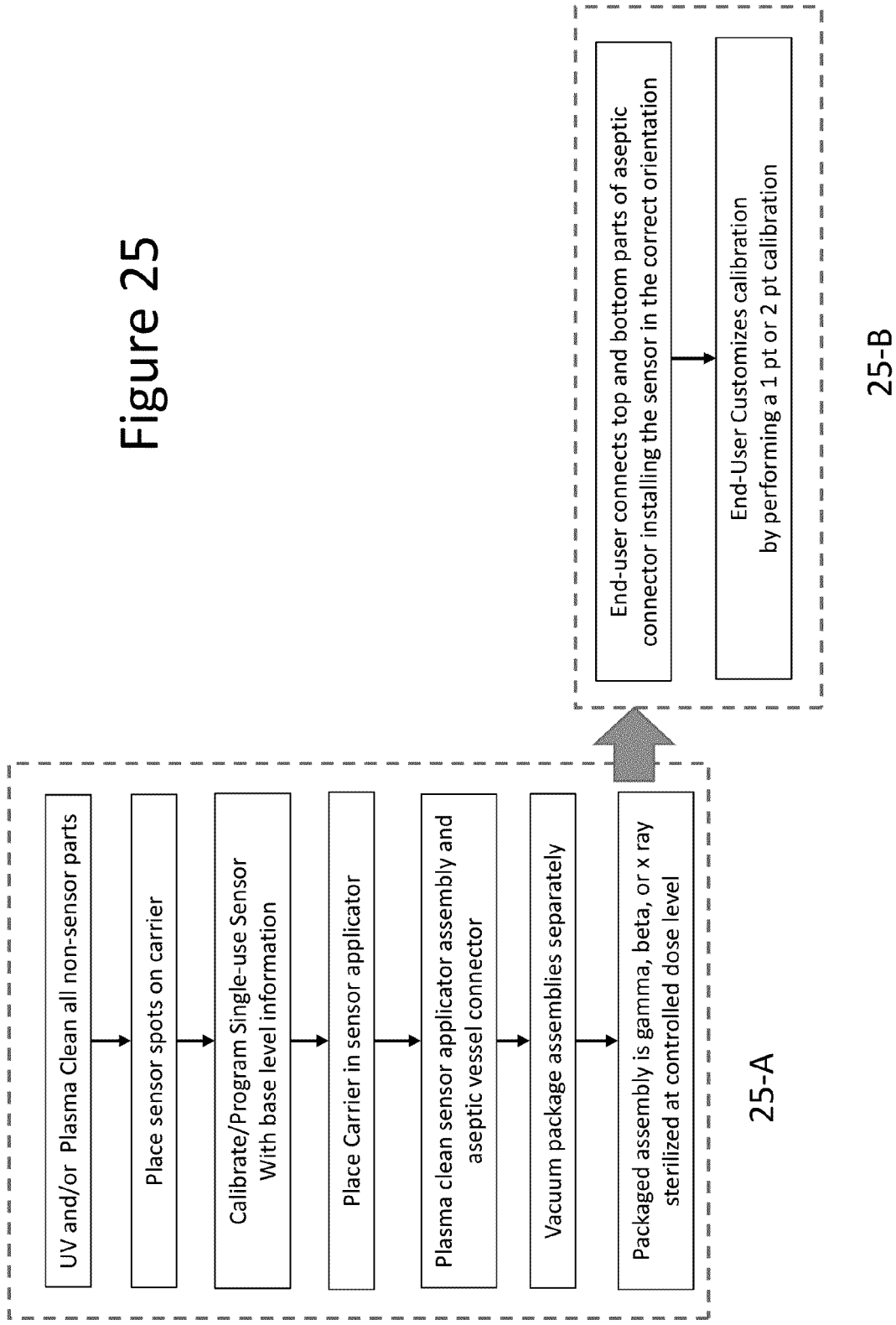
FIG. 25 shows a flow chart detailing the method for inserting the sheaths for inserting single-use sensors into single-use bioprocess vessels utilizing the aseptic connector described here.

If the number of CFU's on the optical carrier and associated aseptic connector can be minimized before being packaged, a lower dose of gamma, beta, or x-ray radiation will be required to meet the acceptable limit on CFU's for use in the pharmaceutical production arena. A method for preparing and installing a sensor while reducing the number of CFU's is outlined in FIG. 24. In box 25-A, the activities carried out during the manufacturing and packaging of the sensors are described in detail. In certain embodiments, all of the activities are performed in a class 10,000 or better clean room. The overall bacterial and adventitious agent level in the clean room will be minimized by vigilant cleaning and exposure to UV light. In certain embodiments, all of the components (except, in general, the opto-chemical sensor materials which can be rapidly degraded by exposure to intense UV radiation)

in the aseptic connection system need to be UV cleaned with UV radiation at ≥20 mJ/cm² and/or plasma cleaned as described in the references provided. The opto-chemical sensor spots are affixed to the carrier. The calibration has assumed to have already been carried out and this calibration information is encoded in the associated memory chip or provided in some other fashion to be available to the end-user. The carrier is assembled make up the sensor applicator with its aseptic connection mechanism and plunger. This entire sensor assembly (e.g: carrier, connector, and plunger) and the aseptic vessel connector portion are also plasma cleaned, if necessary, to further reduce the number of colony forming units. Both of the matching components/assemblies are then vacuum packaged in the clean room as per the requirements of the end-user. In certain embodiments, the base packaging material is not light transmitting and meets all the aforementioned requirements of being USP Class VI/ISO10993, animal component derived free, latex free, phthalate free, and sterilizing radiation (e.g.: gamma, beta, x-ray) stable. Stable here means that it does not release agents that have a deleterious effect on the sensors or are toxic and maintain their integrity as packaging materials. Both components/assemblies are now sent for sterilization. A suitable source is e-beam (Beta) radiation, which can be easily controlled. In certain embodiments, the dose will be ≤about 15 kGy as the sensors are minimally affected by this level. However, if higher doses are required, this method of preparation and radiation may minimize the required dose and will decouple of the radiation/sterilization process of the opto-chemical sensor from radiation/sterilization process of the single-use bioprocess vessel. This also eliminates the exposure of the opto-chemical sensor to the free radicals and chemicals produced during the radiation of the single-use bioprocess vessel. If these free radicals are present long (e.g., days to weeks) after the sterilization of the single-use bioprocess vessel, the vessels can be flushed with air, nitrogen, or even water for injection before the aseptic connection between the two components. FIG. 25-B shows the actions of the end-user who receives both the single-use bioprocess container and the sensor applicator assembly. The single-use bioprocess vessel will need to have had the aseptic bioprocess vessel connector attached during its construction. For a flexible film based single-use bioprocess vessel this would likely have entailed having the aseptic vessel connector side be equipped with a plate or flange that was welded to the inner layer during its construction. The end user will connect the sensor applicator as described before, but can orient the sensor if desired. Once the aseptic connection is made the user can perform a 1 point standardization or a 2 point calibration as desired and according to the requirements of the sensor being used.

Depending on the rates of infection (base level of CFU's) found on the components, the UV radiation may not be necessary or not at the above stipulated levels.

This hermetically packaged sensor and carrier can then be exposed to the minimal amount of gamma, beta, or x-ray radiation required to meet the number of CFU as stipulated by ISO 11137. In certain embodiments, a goal is to use ≤15 kGy of radiation to ensure compliance with ISO 11137, at which dose level the effect on opto-chemical sensors may be negligible. Generally, speaking there exist several possible combinations of treatment that can allow compliance with ISO 11137. These include:

1. Gamma/beta/x-ray sterilization of the sealed aseptic connector packages at ≥25 kGy
2. Use of UV Sterilization of the optically insensitive components as described above
3. Use of cold atmospheric plasma of the assemblies in the package or before packaging
4. Exposure of components to ethylene oxide sterilizing compound before packaging if the sensor components are not deleteriously affected by this
5. Any combination of 2, 3, 4, or any combination including step 1 but without the stipulation that the sterilizing radiation exceed 25 kGy.

The sensor carriers from Finesse Solutions, Inc. already come with a base level of calibration already programmed into the attached memory chip. This calibration is developed by detailed testing of similar opto-chemical sensors after running them through the exact same process and often contemporaneously. This calibration may be applied to the balance of the carriers and sensors in the lot that is being processed. This calibration may be applied prior to UV or plasma sterilization and carriers, as they need to be connected to a programming device.

With the sterilization of the single-use vessel and the sensor(s) and its carrier separated, the process for installing of the sensor by the end-user is different than when the two components are sterilized together. In the case of separated sterilization, the sensors may be put on their carriers and processed as described above. The packaged sensors and carriers may be sent out for gamma, e-beam, or x-ray sterilization at ~15 kGy and stored by the vendor (e.g.: Finesse Solutions, Inc.) or sent out for sterilization as orders arrive. As the sensor applicator assembly may be dimensionally small (e.g., <~15 cm) the use of Beta radiation/e-beam is applicable. All of the components can be placed flat, once component deep, such that the sterilizing radiation can be delivered quickly, uniformly, and consistently. Meanwhile, the end-user receives their single-use bio-process vessel from their preferred vendor already gamma irradiated according to that vendor's standards. The single-use bioprocess vessel aseptic connector is already in-place and sterilized with the single-use bio-processing vessel. The single-use vessel is then set-up according to the vendor's instructions. At this point, before filling the vessel with media, the sensor, applicator, and aseptic single-use vessel connector are connected to the vessel as described above. The media is then added and the single-use bio-processing vessel is prepared for initial use. As part of the set-up it is typical for offline samples to be taken so that the dissolved oxygen and pH probes can be standardized to the probes that the process was developed with. At this point, a one-point standardization against the offline standard is typically performed and the sensors are calibrated and ready to use. The temperature is often checked or standardized in a similar manner against a known temperature standard using a port designed into the bag for this purpose.

For example, the carrier for the spots can be "pre-sterilized" using a plasma cleaner and/or using ultra-violet light before and/or after attaching the spots. The ultra-violet light can be supplied by a variety of different high pressure lamps and/or UV LEDs as mentioned above. The choice of sterilization procedure depends on the spots' sensitivity to these sterilization processes. Pre-sterilization may reduce the required gamma or beta dose levels while ensuring that the level of CFU's is acceptable to meet the needs for bioprocessing or similar activity. Typical gamma sterilization facilities use $CO_{60}$ to provide the gamma radiation, and providing a uniform dose across a palette is not possible, nor is delivering a precise dose.

Due to this fact, x-ray (e.g. Rhodotron), or beta radiation may be a suitable alternative to gamma radiation for sterilization of the optical spot and carrier. As mentioned before, beta radiation does not penetrate as far into materials as gamma radiation does, but an accelerator source typically allows for far less ambiguity in dosing than gamma sources. Due to the lack of penetration depth, beta radiation is rarely used for sterilizing single-use vessels in a commercial setting. It simply is not economical to sterilize each individual single-use vessel separately and if the container exceeds 12"-18", the beta radiation will not thoroughly or uniformly sterilize the vessel.

A typical free space optical "carrier" or component for the spots would not reach a size that cannot be uniformly sterilized by with beta radiation, and they can be packaged such that they are in a thin (less than 5 inches) layer which can be quickly and economically sterilized. Additionally, the dose of radiation required to meet ISO11137-2 standards for the reduction in the number of colony forming units (CFU's) of bacteria can be dramatically reduced by adherence to the correct process. An example process allowing this reduction carries out all of the work in a 1000 clean room or better and pre-sterilizing the carrier using both Ultra Violet (UV) radiation and plasma cleaning UV radiation is widely documented and is widely used for disinfection (e.g.: *Ultraviolet Disinfection Guidance Manual For The Final Long Term 2 Enhanced Surface Water Treatment Rule*, US EPA, Office of Water (4601), EPA 815-R-06-007, incorporated herein by reference). Plasma cleaning has also been found to be an effective agent for sterilization (e.g.: *Cold Atmospheric Air Plasma Sterilization against Spores and Other Microorganisms of Clinical Interest*, Klampfl et al. Applied and Environmental Microbiology, 78, 15, 5077, August 2012, previously incorporated by reference).

We have found experimentally that if the spots are affixed to a carrier made of a suitable material (e.g., a material that does not outgas even when exposed to gamma radiation) and packaged in a suitable material, radiation and the dose of sterilizing radiation can be maintained at ≤about 15 kGy there is little to no damage done to the spots. At this level of radiation, the change in the phase response of the spots is minimized and is very repeatable. In our experiments using suitable materials we have found that there is no outgassing during the sterilization process or at least none that affects the spots. Therefore many of the negative effects that sensors endure during gamma sterilization can be avoided.

The pre-sterilization of the carrier can be carried out with UV light, for example with a pulsed Xenon lamp or other source that has the peak of its radiation between 254 nm and 280 nm with sufficient intensity. Other sources as mentioned above are high power UV LEDs, and other high pressure metal vapor lamps (e.g. Mercury) or laser sources.

Additional applications of this type of aseptic connector can be found for radiation (gamma, beta, x-ray) sensitive electronics. Many types of digital (and analog) chips/circuits cannot be utilized in single-use bioprocess vessels due to their incompatibility with the sterilization process. Specifically, most integrated circuits are not compatible with sterilization by the aforementioned ionizing radiation. If the circuits, potentially, containing other types of sensors (e.g. pressure, temperature) which have their signal conditioned by integrated circuit electronics are desired to be implemented on a single-use bio-process vessel, they can also be mounted on a carrier and sterilized with UV radiation, atmospheric plasma, or chemical processing (e.g. ethylene oxide). Similarly, the peripheral components mentioned earlier such as sampling ports, temperature sensing wells, or additional spargers can all be added to a single-use bioprocessing vessel post sterilization this way, leading to a far more flexible component for the end user.

What is claimed is:

1. An aseptic peripheral connection assembly for installing a sterilized peripheral in a bio-processing vessel via an aseptic connector affixed to the vessel, the peripheral connection assembly comprising:
   a. a carrier within an applicator sleeve, the carrier comprising the sterilized peripheral and a first sealing member configured to form a leak-tight seal with the aseptic vessel connector on the bio-processing vessel at a location where the carrier is to be installed;
   b. an applicator comprising the applicator sleeve and a vessel-facing opening adjacent to an applicator connector configured to temporarily connect to the aseptic vessel connector on the bio-processing vessel;
   c. a plunger within the applicator sleeve and configured to plunge the carrier from a position within the applicator sleeve to a position engaged with the aseptic vessel connector to form the leak-tight seal, wherein the plunger comprises a second sealing member; and
   d. a removable hermetic sealing tab covering the vessel-facing opening of the applicator sleeve to maintain the sterilized peripheral in aseptic condition prior to installation in the bio-processing vessel.

2. The aseptic peripheral connection assembly of claim 1, wherein the bio-processing vessel is a self-contained container or a flow path.

3. The aseptic peripheral connection assembly of claim 1, wherein the bio-processing vessel is a bioreactor or a filter flow path.

4. The aseptic peripheral connection assembly of claim 1, wherein the peripheral is a single use sensor.

5. The aseptic peripheral connection assembly of claim 1, wherein the carrier comprises two or more sensors.

6. The aseptic peripheral connection assembly of claim 1, wherein the carrier is disk shaped with a sensor having an exposed sensing surface on a flat side of the carrier.

7. The aseptic peripheral connection assembly of claim 6, wherein the carrier comprises two or more sensors having exposed sensing surfaces on a flat side of the carrier.

8. The aseptic peripheral connection assembly of claim 1, wherein the carrier is generally sheath shaped and comprises a sensor having an exposed sensing surface on an end of the carrier.

9. The aseptic peripheral connection assembly of claim 1, wherein the first sealing member comprises a clip or a ledge.

10. The aseptic peripheral connection assembly of claim 1, wherein the first sealing member comprises an o-ring.

11. The aseptic peripheral connection assembly of claim 1, wherein the applicator sleeve is constructed of a rigid material.

12. The aseptic peripheral connection assembly of claim 1, wherein the applicator is configured to be removed from the carrier and the bio-processing vessel after the carrier is installed in the bio-processing vessel.

13. The aseptic peripheral connection assembly of claim 1, wherein the applicator sleeve has a tubular shape and the plunger has a substantially circular shape comprising the second sealing member that forms a seal with an interior surface of the applicator.

14. The aseptic peripheral connection assembly of claim 1, wherein the applicator connector comprises a clip or a ledge.

15. The aseptic peripheral connection assembly of claim 1, wherein the applicator connector comprises an o-ring.

16. The aseptic peripheral connection assembly of claim 1, wherein the applicator connector is configured to provide a hermetic seal with the aseptic vessel connector while the plunger inserts the carrier into the aseptic vessel connector.

17. The aseptic peripheral connection assembly of claim 1, wherein the applicator is composed of a polycarbonate, polysulfone, polyvinylidene fluoride, co-polyester, or a combination of any of these.

18. The aseptic peripheral connection assembly of claim 1, wherein the applicator is composed of USP Class VI material that is animal derived component free, latex free, phthalate free, and gamma and e-beam stable.

19. The aseptic peripheral connection assembly of claim 1, wherein the second sealing member comprises an o-ring for forming a hermetic seal with the applicator sleeve while plunging the carrier into position with the aseptic vessel connector.

20. The aseptic peripheral connection assembly of claim 1, wherein the removable hermetic sealing tab is configured to be removed from the aseptic peripheral connection assembly after connecting the applicator to the aseptic vessel connector on the bio-processing vessel at a location where the sterilized peripheral is to be installed, and before plunging the carrier from a position within the applicator sleeve to a position engaged with the aseptic vessel connector.

21. The aseptic peripheral connection assembly of claim 1, wherein the removable hermetic sealing tab comprises a film or sheet having a thickness of between about 1 mil and 20 mil.

22. The aseptic peripheral connection assembly of claim 1, wherein the removable hermetic sealing tab comprises a USP Class VI, latex free, phthalate free animal derived component free polymeric plate.

23. The aseptic peripheral connection assembly of claim 1, wherein the removal hermetic sealing tab is coated with an adhesive.

24. A bio-processing vessel kit comprising:
   a. the aseptic peripheral connection assembly of claim 1; and
   b. a bio-processing vessel housing with the aseptic vessel connector affixed.

25. The bio-processing vessel kit of claim 24, wherein the bio-processing vessel housing is a single use bio-processing vessel housing or a flow path.

26. The bio-processing vessel kit of claim 24, wherein the bio-processing vessel housing is configured or designed as a bioreactor or a filter with a flow path.

27. The bio-processing vessel kit of claim 26, wherein the bio-processing vessel housing comprises a container packed with material for product separation.

28. A method of fabricating an aseptic peripheral connection assembly for installing a sterilized peripheral in a bio-processing vessel via an aseptic connector affixed to the vessel, wherein the aseptic peripheral connection assembly comprises (i) a carrier within an applicator sleeve, the carrier comprising the peripheral and a sealing member configured to form a leak-tight seal with the aseptic vessel connector on the bio-processing vessel at a location where the carrier is to be installed; and (ii) an applicator comprising the applicator sleeve and vessel-facing opening adjacent to an applicator connector configured to temporarily connect to the aseptic vessel connector on the bio-processing vessel, the method comprising:
   a. placing the carrier in the applicator;
   b. packaging the aseptic peripheral connection assembly in a hermetically sealed package; and
   c. sterilizing the aseptic peripheral connection assembly, wherein the sterilizing does not employ exposure to radiation at a level of greater than about 15 kGy.

29. A method of using an aseptic peripheral connection assembly for installing a sterilized peripheral in a bio-processing vessel via an aseptic connector affixed to the vessel, wherein the aseptic peripheral connection assembly comprises (i) a carrier within an applicator sleeve, the carrier comprising the peripheral and a sealing member configured to form a leak-tight seal with the aseptic vessel connector on the bio-processing vessel at a location where the carrier is to be installed; and (ii) an applicator comprising the applicator sleeve and vessel-facing opening adjacent to an applicator connector, the method comprising:
   a. connecting the applicator connector of the applicator to the aseptic vessel connector on the bio-processing vessel;
   b. removing a hermetic sealing tab covering the vessel-facing opening of the applicator sleeve; and
   c. plunging the carrier from a position within the applicator sleeve to a position engaged with the aseptic vessel connector, and forming the leak-tight seal therewith.

* * * * *